United States Patent
Bell et al.

(10) Patent No.: US 9,402,986 B2
(45) Date of Patent: Aug. 2, 2016

(54) METHOD FOR HERNIA REPAIR

(71) Applicant: Insightra Medical, Inc., Irvine, CA (US)

(72) Inventors: Stephen Graham Bell, Rome (IT); Wayne A. Noda, Mission Viejo, CA (US); Giuseppe Amato, Palermo (IT)

(73) Assignee: Insightra Medical, Inc., Irvine, CA (US)

( * ) Notice: Subject to any disclaimer, the term of this patent is extended or adjusted under 35 U.S.C. 154(b) by 0 days.

(21) Appl. No.: 14/515,975

(22) Filed: Oct. 16, 2014

(65) Prior Publication Data
US 2015/0038782 A1    Feb. 5, 2015

Related U.S. Application Data

(60) Division of application No. 13/476,202, filed on May 21, 2012, now Pat. No. 8,940,017, which is a continuation-in-part of application No. 12/183,930, filed on Jul. 31, 2008.

(60) Provisional application No. 61/030,439, filed on Feb. 21, 2008, provisional application No. 61/013,619, filed on Dec. 13, 2007.

(51) Int. Cl.
*A61F 2/04* (2013.01)
*A61M 39/06* (2006.01)
(Continued)

(52) U.S. Cl.
CPC ........ *A61M 39/0613* (2013.01); *A61B 17/3423* (2013.01); *A61B 17/3468* (2013.01);
(Continued)

(58) Field of Classification Search
CPC ....................................................... A61F 2/04

USPC ........... 600/37, 204, 206, 208, 217; 606/213, 606/201, 151, 230, 119, 144, 145
See application file for complete search history.

(56) References Cited

U.S. PATENT DOCUMENTS

| 2,738,790 A | 3/1956 | Todt, Sr. et al. |
| 4,188,945 A | 2/1980 | Wenander |

(Continued)

FOREIGN PATENT DOCUMENTS

| WO | 9800069 | 1/1998 |
| WO | 9800068 A9 | 7/1999 |

(Continued)

OTHER PUBLICATIONS

Stephen Graham Bell, Guieseppe Amato, "Implant for Hernia Repair", related pending U.S. Appl. No. 14/255,446, non-final office action dated Dec. 16, 2015.

(Continued)

*Primary Examiner* — Vy Bui
(74) *Attorney, Agent, or Firm* — John L. Rogitz

(57) ABSTRACT

A hernia repair implant includes a first layer for facing a body structure having a hernia defect to cover the defect while promoting tissue growth into the first layer from the body structure. The implant also includes a second layer opposed to the first layer and made of anti-adhesion material to prevent growth of tissue into the second layer from body structures contacting the second layer. Furthermore, the implant includes at least one engagement strap connected to the first layer and extending therefrom to terminate at a free end. The engagement strap defines opposed thin edges and opposed flat surfaces extending between the edges. At least one barb extends from at least one edge and/or at least one flat surface of the strap and is configured to impede motion of the strap in only a single direction.

12 Claims, 21 Drawing Sheets

(51) Int. Cl.
*A61F 2/00* (2006.01)
*A61B 17/34* (2006.01)
*A61B 19/00* (2006.01)
*A61M 39/02* (2006.01)
*A61B 17/00* (2006.01)

(52) U.S. Cl.
CPC ........... *A61B19/5202* (2013.01); *A61F 2/0063* (2013.01); *A61M 39/02* (2013.01); *A61B 2017/00358* (2013.01); *A61B 2017/00362* (2013.01); *A61B 2017/00889* (2013.01); *A61B 2017/00951* (2013.01); *A61B 2017/3419* (2013.01); *A61B 2017/3466* (2013.01); *A61F 2002/0072* (2013.01); *A61M 2039/066* (2013.01); *A61M 2039/0673* (2013.01)

(56) References Cited

U.S. PATENT DOCUMENTS

| | | | |
|---|---|---|---|
| 5,219,358 | A | 6/1993 | Bendel et al. |
| 5,337,736 | A | 8/1994 | Reddy |
| 5,366,460 | A * | 11/1994 | Eberbach ............ A61B 17/0057 128/887 |
| 5,431,323 | A | 7/1995 | Smith et al. |
| 5,458,609 | A | 10/1995 | Gordon et al. |
| 5,640,977 | A | 6/1997 | Leahy et al. |
| 5,716,367 | A | 2/1998 | Koike et al. |
| 5,810,721 | A | 9/1998 | Mueller et al. |
| 5,853,395 | A * | 12/1998 | Crook ................ A61B 17/3423 600/208 |
| 5,899,909 | A | 5/1999 | Claren et al. |
| 5,972,022 | A | 10/1999 | Huxel |
| 6,332,888 | B1 | 12/2001 | Levy et al. |
| 6,382,214 | B1 | 5/2002 | Raz et al. |
| 6,383,201 | B1 | 5/2002 | Dong |
| 6,451,032 | B1 | 9/2002 | Ory et al. |
| 6,475,135 | B1 | 11/2002 | Levy |
| 6,911,003 | B2 | 6/2005 | Anderson et al. |
| 6,936,054 | B2 | 8/2005 | Chu |
| 6,939,296 | B2 * | 9/2005 | Ewers ....................... A61B 1/06 128/849 |
| 6,984,237 | B2 | 1/2006 | Hatch et al. |
| 6,991,637 | B2 | 1/2006 | Crawley et al. |
| 7,101,381 | B2 | 9/2006 | Ford et al. |
| 7,131,943 | B2 | 11/2006 | Kammerer |
| 7,229,453 | B2 | 6/2007 | Anderson et al. |
| 7,338,502 | B2 | 3/2008 | Rosenblatt |
| 7,404,819 | B1 | 7/2008 | Darios et al. |
| 7,785,334 | B2 | 8/2010 | Ford et al. |
| 2002/0103494 | A1 | 8/2002 | Pacey |
| 2002/0151762 | A1 | 10/2002 | Rocheleau et al. |
| 2003/0176762 | A1 | 9/2003 | Kammerer |
| 2003/0192553 | A1 | 10/2003 | Rambo |
| 2004/0015155 | A1 | 1/2004 | Whalen et al. |
| 2004/0039453 | A1 | 2/2004 | Anderson et al. |
| 2004/0054353 | A1 | 3/2004 | Taylor |
| 2004/0068159 | A1 | 4/2004 | Neisz et al. |
| 2004/0144395 | A1 | 7/2004 | Evan et al. |
| 2004/0221431 | A1 | 11/2004 | Wittmann |
| 2005/0004576 | A1 | 1/2005 | Benderev |
| 2005/0250977 | A1 | 11/2005 | Montpetit et al. |
| 2006/0058575 | A1 | 3/2006 | Zaddem et al. |
| 2006/0083767 | A1 | 4/2006 | Deusch et al. |
| 2006/0205995 | A1 | 9/2006 | Browning |
| 2006/0258898 | A1 | 11/2006 | Montpetit et al. |
| 2006/0276908 | A1 | 12/2006 | Sogaard-Andersen et al. |
| 2006/0282105 | A1 | 12/2006 | Ford et al. |
| 2007/0239208 | A1 | 10/2007 | Crawford |
| 2007/0260179 | A1 | 11/2007 | Sholev et al. |
| 2007/0270890 | A1 | 11/2007 | Miller |
| 2008/0065229 | A1 | 3/2008 | Adams |
| 2008/0081945 | A1 | 4/2008 | Toso et al. |
| 2008/0109015 | A1 | 5/2008 | Chu et al. |
| 2008/0132753 | A1 | 6/2008 | Goddard |
| 2008/0135753 | A1 | 6/2008 | Yamashita et al. |
| 2008/0147200 | A1 | 6/2008 | Rousseau et al. |
| 2008/0200751 | A1 | 8/2008 | Browning |
| 2008/0269896 | A1 | 10/2008 | Cherok et al. |
| 2009/0171142 | A1 | 7/2009 | Chu |
| 2009/0192530 | A1 | 7/2009 | Adzich et al. |
| 2009/0198260 | A1 | 8/2009 | Ford et al. |
| 2009/0216253 | A1 | 8/2009 | Bell et al. |
| 2009/0240267 | A1 | 9/2009 | Crawley et al. |
| 2011/0130774 | A1 | 6/2011 | Criscuolo et al. |
| 2011/0184429 | A1 | 7/2011 | Saldinger |
| 2011/0276090 | A1 | 11/2011 | Berndt et al. |
| 2011/0295283 | A1 | 12/2011 | Darois et al. |
| 2012/0004501 | A1 | 1/2012 | Beyer |
| 2012/0116425 | A1 * | 5/2012 | Intoccia ................ A61F 2/0045 606/151 |

FOREIGN PATENT DOCUMENTS

| | | |
|---|---|---|
| WO | 03096929 | 11/2003 |
| WO | 2004012579 | 2/2004 |
| WO | 2006110274 A2 | 11/2005 |
| WO | 2006108145 | 10/2006 |
| WO | 2007016698 | 2/2007 |
| WO | 2007109508 | 9/2007 |
| WO | 2007149348 | 12/2007 |
| WO | 2010039249 A1 | 4/2010 |
| WO | 2010141321 A1 | 12/2010 |

OTHER PUBLICATIONS

Stephen Graham Bell, Guiseppe Amato, "Implant for Hernia Repair", related pending U.S. Appl. No. 14/255,446, applicants response to non-final office action filed Dec. 16, 2015.

Stephen Graham Bell, Wayne A. Noda, Giuseppe Amato, "Implant for Hernia Repair", related pending U.S. Appl. No. 14/516,005, Non-Final Office Action dated Feb. 25, 2016.

Stephen Graham Bell, Giuseppe Amato, "Implant for Hernia Repair" file history of related pending U.S. Appl. No. 14/255,446, filed Apr. 17, 2014.

Stephen G. Bell, Wayne A. Noda, Giuseppe Amato, "Methods and Apparatus for Treating Ventral Wall Hernia" file history of related pending U.S. Appl. No. 12/183,930, filed Jul. 31, 2008.

Stephen Graham Bell, Giuseppe Amato, "Implant for Hernia Repair" file history of related pending U.S. Appl. No. 13/443,266, filed Apr. 10, 2012.

Stephen Graham Bell, Wayne A. Noda, Giusseppe Amato, "Implant for Hernia Repair" file history of related pending U.S. Appl. No. 14/515,915, filed Oct. 16, 2014.

Stephen Graham Bell, Wayne A. Noda, Giuseppe Amato, "Implant for Hernia Repair" file history of related pending U.S. Appl. No. 14/515,946, filed Oct. 16, 2014.

Stephen Graham Bell, Wayne A. Noda, Giuseppe Amato, "Implant for Hernia Repair" file history of related pending U.S. Appl. No. 14/516,005, filed Oct. 16, 2014.

Stephen Graham Bell, "Hernia Repair Device with Core and Advanced Pre-Peritoneal Disk Deployment" file history of related U.S. Appl. No. 14/452,916, filed Aug. 6, 2014.

* cited by examiner

METHOD FOR HERNIA REPAIR

This application is a continuation in part of U.S. patent application Ser. No. 12/183,930, filed Jul. 31, 2008 and published as USPP 2009/0216253, incorporated herein in its entirety.

FIELD OF THE APPLICATION

The present application relates generally to the repair of defects in muscular structures, and more particularly to implants to address ventral wall hernias, inguinal hernias, and methods for advancing the implants into a patient less invasively.

BACKGROUND OF THE INVENTION

The above-referenced patent publication discloses a surgical implant with both a tension free and fixation free implant mesh having multiple straps extending radially outward from the implant mesh. The strap are pulled through the ventral (abdominal) wall musculature to fix the implant mesh to the ventral wall such that when implanted the implant mesh is in a slackened condition relative to the ventral wall. The implant mesh is sized to be substantially larger than the hernia. To permit tissue ingrowth from the ventral wall into the mesh while preventing undesirable ingrowth of structures in the peritoneal space such as the bowel into the mesh, the mesh is backed with an anti-adhesion layer or substance. A non-adhesion mesh can be used in the pre-peritoneal space.

While the structures in the above-referenced patent publication prove effective, present principles understand that delivering the mesh laparoscopically, positioning the mesh within the patient and indicating locations outside the patient at which strap retrieval tools should be advanced, and securing strap fixation within the patient all pose challenges that are addressed herein.

SUMMARY OF THE INVENTION

Accordingly, in one embodiment a hernia repair implant includes a first layer for facing a body structure having a hernia defect to cover the defect while promoting tissue growth into the first layer from the body structure. The implant also includes a second layer opposed to the first layer that is made of anti-adhesion material to prevent growth of tissue into and/or prevent adhesions with the second layer from body structures such as abdominal viscera contacting the second layer. Furthermore, the implant includes at least one engagement strap connected to the first layer and extending therefrom to terminate at a free end. Note that the engagement strap defines opposed thin edges and opposed flat surfaces extending between the edges. Additionally, at least one barb extends from at least one edge and/or at least one flat surface of the strap and is configured to impede motion of the stop in only a single linear direction.

If desired, the strap may include plural barbs that may each extend away from a respective edge of the strap. Even further, it is to be understood that there may be plural straps connected to the first layer. In some embodiments, the barb may be a thin filament oriented at an oblique angle relative to a long axis of the strap. Also in some embodiments, the barb may be generally triangular and may be oriented on the strap parallel to a long axis of the strap. Further still, if desired the barb may extend away from at least one edge of the strap and/or the barb may extend away from a flat surface of the strap.

In another aspect, a pneumatic seal for laparoscopic surgery includes a patient adhesion side positionable against a patient's insufflated abdomen to hold the seal onto the patient. The seal also includes a puncture membrane opposed to the patient adhesion side. In addition to the above, the seal includes a sealant chamber containing sealant that is disposed under the puncture membrane. Thus, a piercing instrument can be advanced through both the puncture membrane and sealant and into the patient's insufflated abdomen with the sealant sealing around the piercing instrument to impede leakage of insufflation gas from inside the patient's abdomen along the piercing instrument to an area external to the patient.

In still another aspect a method for laparoscopic implantation of a hernia repair implant having fixation straps with respective ends includes laying the implant, or a pattern thereof, on a patient's abdomen. The method then includes indicating on the pattern's abdomen respective strap end retrieval piercing locations for at least some respective strap ends. Then the method includes advancing the implant into the patient's insufflated abdomen through a trocar and unfolding the implant inside the patient. Thereafter, the method includes using the piercing locations indicated on the patient's abdomen, retrieving snaps up into the patient's tissue by advancing a snaring instrument into the patient through a piercing location, snaring the end of the strap, and pulling the strap outwardly.

In yet another aspect, a method for laparoscopic implantation of a hernia repair implant having fixation straps with respective ends includes advancing the implant into the patient's insufflated abdomen through a trocar and unfolding the implant inside the patient. The method also includes retrieving a strap up into the patient's tissue by first advancing a snaring instrument into the patient along a path that is not parallel to an anterior-posterior dimension defined by the patient's body and then snaring the end of the strap using the snaring instrument. The method then includes pulling the strap outwardly along the path such that the strap is disposed in the patient in an orientation not parallel to the anterior-posterior dimension. Thereafter, the method includes disengaging the instrument from the strap such that at least a segment of the strap remains implanted in the patient in the orientation not parallel to the anterior-posterior dimension.

In still another aspect, a snaring instrument for snaring a strap of a hernia repair implant disposed in a patient's abdomen includes an elongated tube assembly defining a distal end segment terminating at an open distal end. The instrument also includes a guide wire opening in the distal end segment for receiving a guide wire therethrough such that the distal end segment can ride along the guide wire extending through the open distal end and guide wire opening. Further still, the tube assembly also defines a proximal segment. The distal and proximal segments are movable relative to each other between a juxtaposed configuration and a separated configuration. In the juxtaposed configuration, the proximal segment is closely juxtaposed with the distal segment and a movable grasping jaw within the assembly is oriented longitudinally within the assembly. In the separated configuration, the proximal segment is distanced from the distal segment to permit the movable grasping jaw within the assembly to assume, under material bias, a grasping position in which the grasping jaw is oriented at an oblique angle relative to a long axis defined by the assembly and a free distal end of the jaw is disposed radially outward of the segments. This permits the strap to be positioned between the jaw and the long axis so that the assembly can then be moved to the juxtaposed configuration to trap the strap for retrieval.

In another aspect, a soaring instrument for snaring a strap of a hernia repair implant disposed in a patient's abdomen includes an elongated tube assembly defining a distal end segment terminating at an open distal end. The instrument also includes a curved hook member pushable out of the distal end. The curved hook member has first and second co-parallel legs joined together by a curved distal bight. It is to be understood that the first, leg terminates at a proximal end. Additionally, the hook member is movable between an extended position and a retracted position. In the extended position, the proximal end of the first leg is exposed such that the strap can be passed proximal to the proximal end of the first leg dispose the strap between the legs. In the retracted position, the proximal end of the first leg is not exposed to trap the strap between the legs for retrieval.

In another aspect, a snaring instrument for snaring a strap of a henna repair implant disposed in a patient's abdomen includes an elongated tube assembly defining a distal end segment terminating at an open distal end. The instrument also includes a snare member extending out of the distal end. The snare member has first and second legs. The first leg is movable between a closed configuration, in which the legs form a completely enclosed loop, and an open configuration, in which a gap is established through the first leg to permit the strap to pass therethrough.

In yet another aspect, a snaring instrument for snaring a strap of a hernia repair implant disposed in a patient's abdomen includes an elongated tube assembly defining a distal end segment. The instrument further includes a magnet disposed on the distal segment to attract a magnet on the strap. Furthermore, the instrument includes a grasping member on the distal end segment movable to grasp and then hold the strap.

In still another aspect, a snaring instrument for snaring a strap of a hernia repair implant disposed in a patient's abdomen and then partially retracting the strap and transecting the strap to reside in patient tissue includes an elongated tube assembly defining a distal end segment terminating in an open distal end. The snaring instrument also includes a hypotube slidably disposed in the assembly. The snaring instrument further includes a loop connected to a loop line disposed in the hypotube. The loop is disposed on a distal end of the hypotube such that pushing the hypotube distally in the assembly pushes the loop out of the open distal end and pulling on the loop line cinches the loop against the distal end of the hypotube to shrink the loop. Furthermore, a guard shaft is also slidably disposed in the assembly and includes a cutter guard/cover on a distal end thereof. The instrument also includes a cutter formed with a cutting edge (e.g., a blade). The cutter is positioned inside the tube assembly at or near the distal end to transect, using the cutting edge, a strap cinched by the loop and retracted into the tube assembly by the loop fine. Thus, note that the guard shaft is slidably movable within the assembly such that the cutter guard covers and hence guards the cutter and cutting edge when the cutter and edge are not transecting the strap.

In another aspect a method for laparoscopic placement of a hernia repair implant includes advancing a hollow tunneling catheter through a patient's skin into an insufflated abdomen of a patient to form a path. The method further includes advancing an illumination catheter through the tunneling catheter. The illumination catheter has a light source at a distal end and/or tip thereof to thus illuminate at least a portion of the illumination catheter to thereby provide a visible indication from inside the abdomen and appreciable outside the patient of the intramuscular position and/or structure of the patient's abdominal wall being transilluminated through tissue layers of the abdominal wall. The illumination catheter is advanced between a fat layer and a muscle layer but not through the muscle layer to a muscle layer piercing location under visualization of light from the light source propagating through the skin. The method then includes removing the illumination catheter from the tunneling catheter and advancing a snare catheter through the tunneling catheter to the piercing location. The snare catheter has a puncturing distal segment pushable out of an open distal end of the snare catheter to assume a curved configuration under material bias. The method then includes advancing the puncturing distal segment through the muscle and fascia layers into the insufflated abdomen to establish a retrieval path through which a portion of the implant can be retrieved.

In yet another aspect, a method for laparoscopic advancement of a hernia repair implant into a patient includes insufflating the abdomen of the patient and establishing laparoscopic access into the abdomen through a trocar assembly. The method further includes pushing a center portion of the implant into an open proximal funnel removably housing a flexible hollow sheath using a grasper such that the center portion of the implant is thus pushed into the sheath inside the funnel. The method then includes continuing to push the implant further into the sheath to cause the implant to fold inwardly on itself as it enters the sheath. The sheath is removed from the funnel and advanced into the trocar assembly.

In another aspect, a snaring instrument for snaring a strap of a hernia repair implant disposed in a pattern's abdomen includes an elongated tube assembly defining a distal end segment terminating at an open distal end. The instrument also includes a curved snare member extending out of the distal end of the assembly and cord attached to the snare member at or near a distal end of the snare member. The cord extends through the assembly to a proximal end segment of the assembly. Furthermore, the snare member and cord are movable between a closed configuration, in which the snare member and cord are proximate to each other and have substantially the same degree of curvature, and an open configuration, in which the snare member and cord are distanced from each other to establish a gap to allow a strap to pass therethrough.

In still another aspect, a method for laparoscopic advancement of a hernia repair implant into a patient includes insufflating the abdomen of the patient and establishing laparoscopic access into the abdomen through a trocar assembly. Then, using a cord, a center portion of the implant may be pulled into an open proximal funnel. The method then includes continuing to pull the implant further into the funnel, thus causing the implant to fold inwardly on itself as it enters the funnel. Then the method includes advancing the funnel with the implant into the trocar assembly.

The details of the present invention, both as to its structure and operation, can best be understood in reference to the accompanying drawings, in which like reference numerals refer to like parts, and in which:

DETAILED DESCRIPTION OF THE PREFERRED EMBODIMENT

Initially, it is to be understood that although the repair of ventral hernias is particularly referenced herein, the apparatus and methods described herein may be used for other surgical or laparoscopic procedures such as, but not limited to, other instances where a tissue structure of the human body requires strengthening and/or supporting. Furthermore, although shown in the ventral portion of the abdominal wall and although so described for treatment of ventral hernias, the apparatus and methods described herein may be used for inguinal hernias, pelvic support, and other procedures and/or areas of the body.

Figure 1A:
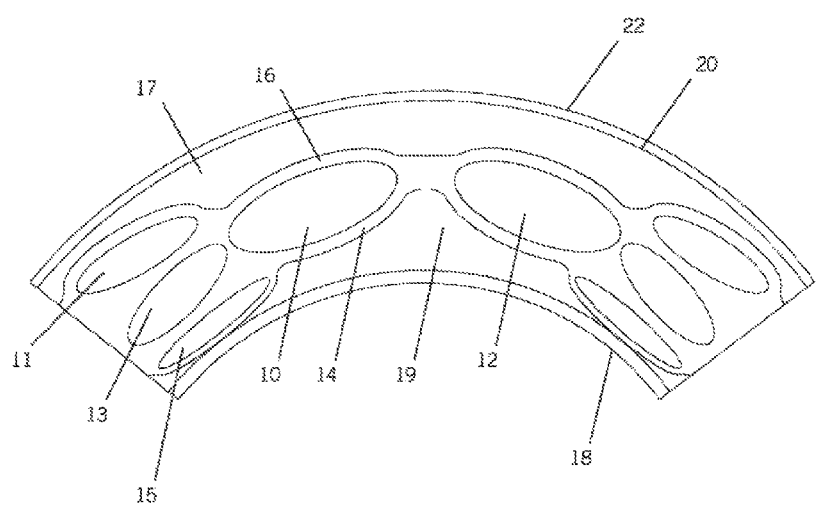
FIG. 1A is a cross-sectional view of a ventral portion of an anterior abdominal wall.

Now initially referring to FIG. 1A, a cross-sectional view of a normal, anterior abdominal wall of the ventral region of the body is shown. As shown, the abdominal, wall includes left and right rectus muscles 10 and 12 enclosed and held in place by posterior layers of fascia 14 and anterior layers of fascia 16. These layers of fascia, which are thin, strong fibrous tissue, merge together in the region intermediate the rectus muscles 10 and 12. Lateral to the rectus muscles 10 and 12 are the external oblique 11, internal oblique 13, and transverse muscle 15. A thin layer 18, called the peritoneum, covers the posterior side of the posterior fascia 12. The peritoneum 18 is a soft, pliable layer of tissue material and provides an enclosure for the intestines and other internal viscera. Anterior to the peritoneum 18 is the preperitoneal fat 19. A layer of skin composed of the sub dermis 20 and dermis 22 covers the subcutaneous fat 17 and exterior of the anterior fascia 16.

Figure 1B:
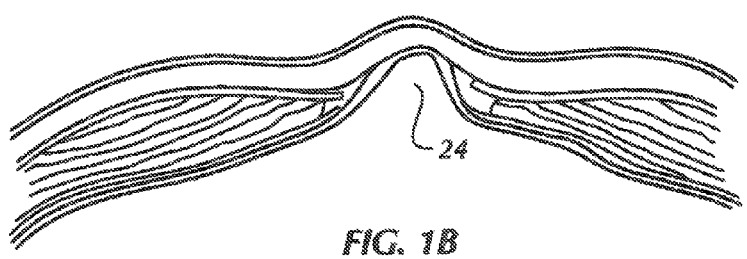
FIG. 1B is a cross-sectional view of FIG. 1A showing a herniation in the ventral wall.

FIG. 1B illustrates a condition where a hernia has formed in the wall of the abdomen. The hernial opening is shown at 24. In this example, the hernia is formed by the rupture of the fascia layers 14 and 16 in the region intermediate the recurs muscles 10 and 12. Note that a visceral protrusion can occur not only in the midline but also in the lateral aspect of the abdominal wall. In this case the viscera protrudes across the lateral wall musculature being composed by the external and internal oblique muscles and the transverse muscles. In any case, the rupture permits the internal viscera to push the peritoneum 18 in an outward direction, creating a bulge 24 in the skin layers 20 and 22. It is to be understood that if not treated, the condition will only worsen with time, with the peritoneal bulge becoming larger.

Now referring to FIGS. 2-5, schematic diagrams illustrating the implantation of a mesh with centering straps are shown. It is to be understood that the figures below generally show methods steps in conjunction with the devices disclosed herein. Thus FIGS. 2-5 show advancing an implant into a patient through an incision adjacent to a portion of a muscle wall to be repaired using a suitable surgical instrument. As shown and described below, the implant includes centering straps connected to a mesh and fixation straps connected to the mesh outboard of where the centering straps are connected. In other words, the centering straps are connected to the mesh closer to the geometric center of the mesh than are the fixation straps. The centering straps are thus advanced through the muscle wall to partially deploy the mesh in a centered positioned relative to a detect in the muscle wall, and the fixation straps are then advanced through the muscle wall to complete the fixation of the mesh to the muscle wall.

With the centering straps, no sutures or other tacking structure need be used to center the mesh over the defect other than the centering straps themselves, which are understood to also fix the mesh to the wall. This advantageously eliminates a separate suturing step during surgery, and furthermore permits improved manipulation when centering the mesh compared to suturing a central part of the mesh on or near the defect since the centering straps permit the surgeon to move the mesh laterally as needed to center the mesh by cinching the straps to center the mesh.

Additionally, note that the meshes described herein, including skeleton mesh portions of the implants described herein and the mesh straps described herein, may be constructed of a solid or a permeable material such that they are receptive to tissue ingrowth. Suitable materials for making the meshes may include, but are not limited to, the following a knitted polypropylene mesh such as that distributed by C. R. Bard, Inc. of Murray Hill, N.J. under the trade name "Marlex"; laminar polypropylene mesh such as that distributed by Dipromed S.r.l. Settimo Torinese Italy, a polyethylene mesh material of the type distributed by E. I. Du Pont de Nemours and Company of Wilmington, Del. under the trade name "Alathon"; a Dacron mesh material or a Nylon mesh material of the type distributed by E. I. Du Pont de Nemours and Company of Wilmington, Del.; Teflon; and silicone.

Additionally, the meshes described herein may be constructed from a metallic mesh or a polymer mesh having interwoven metallic filaments if desired. These filaments may provide additional strength to the meshes and/or make the meshes radiopaque for later visualization. The meshes may be a single layer or have a multilayer construction. The meshes may have one or more layers constructed from a bioabsorbable material such that the meshes may be reabsorbed by the body over time.

Figure 2:
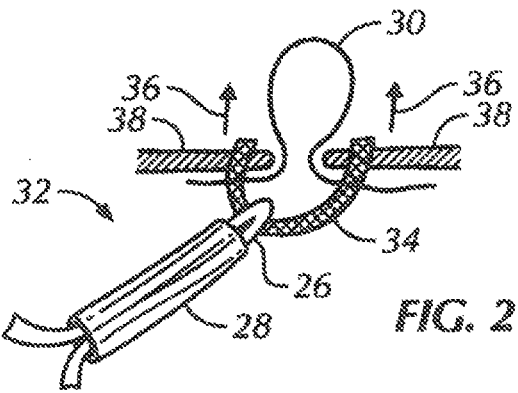
FIGS. 2-5 are schematic diagrams illustrating the implantation of a mesh with centering straps.

Now particularly with respect to FIG. 2, it may be appreciated that an implant 26 has been advanced into a patient through, e.g., an incision next to a hernia 30 to be repaired using a suitable medical device 28 (such as, e.g., a trocar and/or protective sheath). It is to be understood that the implant 26 as shown in FIG. 2 is compressed (e.g., rolled in a cigar-style fashion) to allow advantageous advancement using the device 28. Compressing an implant such as the implant 26 into a device such as the device 28 will be described further below in reference to FIGS. 46-49. Regardless, the implant 2b can be advanced info the patient using, e.g., laparoscopic techniques and toward the hernia 30 in the ventral wall via the abdominal cavity 32. The hernia 30 has characteristics related to/similar to the hernial opening 24 described above. It may be appreciated from FIG. 2 that the implant 26 can include plural centering straps 34.

If desired, the centering straps 34 may be advanced into the patient first, with the remaining portions of the implant delivered via, e.g., the trocar and sheath, after the straps 34 have been at least partially advanced into the patient having the hernia 30. Advancing the straps 34 first may make advancement of the straps 34 into the abdominal wall 38 less complicated since, e.g., the remaining portions of the implant 36 are less likely to get in the way and obscure a surgeon's view while performing a procedure in accordance with present principles and anchoring the centering straps 34 to place the implant 26 at a desired orientation.

As may be appreciated from the upward arrows 36 shown in FIG. 2, the centering straps 34 are advanced at least partially into the abdominal wall 38. If desired, the centering straps 34 may be advanced completely through the abdominal wall 38 such that they are advanced outwardly through the skin of the patient having the hernia 30, including being advanced through the sub dermis and dermis.

Figure 3:
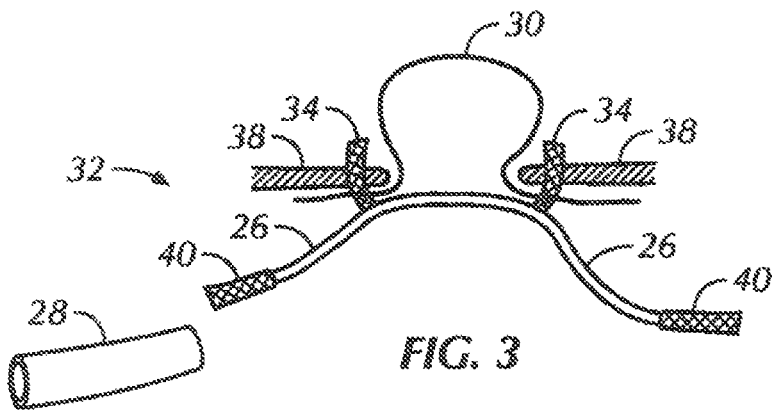

Accordingly, it may be appreciated from FIG. 3 that the centering straps 34 are at least partially disposed in the abdominal wall 38 and, owing to being advanced into the abdominal wall 38 at a location radially distant from the hernia 30 itself, the straps 34 at least partially ensure that no excess mesh or other portion of the implant 26 migrates up into the hernia 30. Furthermore, when advanced into the abdominal wall 38, the straps 34 prevent the implant 26 from sagging when, e.g., pneumoperitoneum is released and thus it at least partially eliminates the chances of hernia recurrence and the potential for seroma. As may also be appreciated from FIG. 3, the device 28 is withdrawn from the area of the hernia 30, allowing the implant 26 to begin to expand, unfold, deploy, and/or otherwise assume its intended shape to cover the defect in the abdominal wall 38 caused by the hernia 30 and facilitate tissue growth in accordance with present principles.

Figure 4:
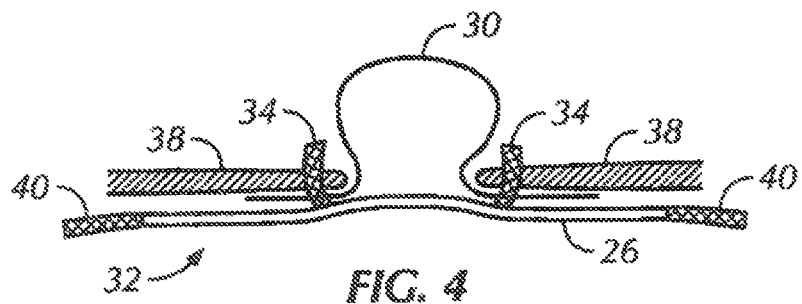

Given that FIG. 3 shows the implant 26 being fully removed from the device 28, it may be appreciated that plural fixation straps 40 are also evident on the implant 26. Example fixation straps 40 will be described further in reference to FIG. 5. But first, note that as shown in FIG. 4, the implant 26 at least partially covers/blocks/obscures the hernia 30 in the abdominal wall 38, it being understood that the implant 26 shown in the configuration of FIG. 4 has at least partially assumed its intended shape.

Figure 5:
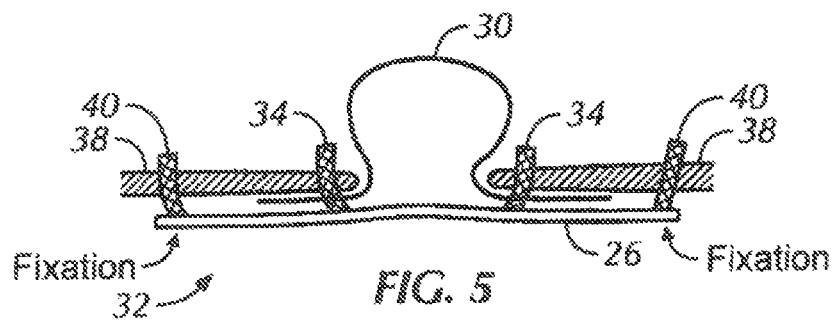

Now in reference to FIG. 5, it may be appreciated that the fixation straps 40 have now been advanced at least partially into the abdominal wall 38. If desired, the fixation straps 40 may be advanced completely through the abdominal wall 38 such that they are advanced through the skin of the patient with the hernia 30. It may be further appreciated from FIG. 5 that a parietal surface of the implant 26 is now disposed against the abdominal wall 38 to fully cover the hernia 30, thereby facilitating tissue growth in accordance with the principles set forth herein while also advantageously blocking passage of objects, fluid, organs, tissue, etc. from passing through the hernia 30 at least partially due to the visceral surface of the implant 26 (which may have anti-adhesion characteristics as set forth herein).

Note that either or both of the centering straps 34 and fixation straps 40 may be secured into abdominal wall 38 by way of friction between the straps 34 and 40 and the wall 38 to minimize patient discomfort while still ensuring that the implant 26 remains in its intended position/orientation, and also does not migrate within the abdominal cavity 32. This provides a relatively tension-free anchoring means while also obviating the need to use other tacking methods that may otherwise provide potential points of adhesion and/or tension during the healing process of the patient, which is undesirable due to, e.g., patient discomfort. Eliminating sutures or other tacking devices also enables the implant to move with expansion or contraction of the surrounding tissue as part of the healing process due to tissue changes over time as the wall 38 heals and as incorporation tissue invades the implant 26. In essence, securing the implant using only strap friction better accommodates tissue movement and/or expansion. However, if deemed necessary additional forms of fixation may nonetheless be used, such as, but not limited to, tacking, sutures, fasteners, and clamps.

Notwithstanding the foregoing, it may be appreciated that using only the friction means of abdominal wall attachment provides a relatively tension-free condition in which the implant 26 is secured into its position with sufficient slack so that as surrounding tissue expands or moves, the implant slack helps avoid pulling and possible tearing of surrounding tissue that may otherwise result from an implant that is secured too tightly or does not have any residual slack due to, e.g., tacking or clamps. Accordingly, it may be appreciated that by virtue of the friction created between the abdominal wall 38 and straps 34 and 40, the straps 34 and 40 secure and stabilize the implant 26 while also permitting a desired level of movement the straps 34 and 40 relative to surrounding tissues over time. The relatively tension-free straps 34 and 40, as well as the configuration of the implant 26 that completely covers the hernia 30, provides for substantial slack allowing for long-term natural abdominal wall remodeling which present principles recognize as being particularly important to reducing and fixing hernias. It is to be understood that this type of tension free and fixation free implant may promote better healing, reduce premature tear-out, dislodgement, or dislocation and provide increased comfort and acceptance by the patient.

Still addressing the straps 34 and 40, note that while FIGS. 2-5 show that the straps 34 and 40 are shown attached to the implant 26 when advanced into the patient having the hernia 30, in other embodiments the implant 26 may be advanced into the abdominal cavity 32 with the straps 34 and 40 unattached thereto. Thus, the straps 34 and 40 may be advanced at least partially into the abdominal wall 38 while unattached from the implant 26 and then subsequently be coupled/attached to the implant 26. Alternatively or in any desired combination, the implant 26 may be advanced into the abdominal cavity 32 with the straps 34 and 40 unattached, and then subsequently the straps may be attached to the implant 26 prior to the straps 34 and 40 being advanced into the abdominal wall 38. It may be appreciated that advantages of advancing the implant 26 into the abdominal cavity 32 with the straps 34 and 40 unattached may be desired for reasons such as, but not limited to, ease of advancement of the implant 26 into the patient (e.g., if the implant is relatively large and difficult to place into or maneuver using the device 28) and ease of placement of the implant 26 against the abdominal wall 28 to thereby cover the hernia 30.

Continuing in reference to the straps 34 and 40, the straps may be made of a mesh such as a polypropylene mesh that facilitates tissue growth in accordance with present principles. The straps 34 and 40 may be made of any other suitable synthetic materials, biological materials, or combination of materials, if desired. Regardless, it is to be understood that to further facilitate advancement of the straps 34 and 40 at least partially into the abdominal wall 38, the straps 34 and 40 may include surgical needles (not shown in FIGS. 2-5) engaged with respective ends of the straps to facilitate advancement of the straps 34 and 40 into the abdominal wall 38. In some embodiments, the needles are removably engaged with the straps 34 and 40 such that the needles may be disengaged with straps 34 and 40 after the snaps 34 and 40 have been at least partially advanced into the abdominal wall.

Also note that in some embodiments, the straps 34 and 40 may be tapered at the ends to be advanced into the abdominal wall 38. This may facilitate advancement of the straps 34 and 40 through various tissue structures. Accordingly, the reduced lateral profile may reduce friction and the resultant force required to, e.g., pull or push the straps 34 and 40 into the abdominal wall 38. The tapered nature may thus, e.g., ease the initial penetration through tissue structures, but once the tapered ends are advanced out of the patient, a firm grasp and/or hold of the strap(s) may be gained by a physician. The wider portion(s) of the strap(s) may then be advanced in accordance with present principles when making adjustments, it being understood that the wider portion(s) are more capable of inducing friction with the abdominal wall, also in accordance with present principles. Note that the straps 34 and 40 may be made out of polyethylene, polypropylene, Teflon, nylon, silicone or other suitable polymer in accordance with present principles that may be useful to reduce friction as the straps 34 and 40 pass through tissue in the abdominal wall 38.

Figure 6:
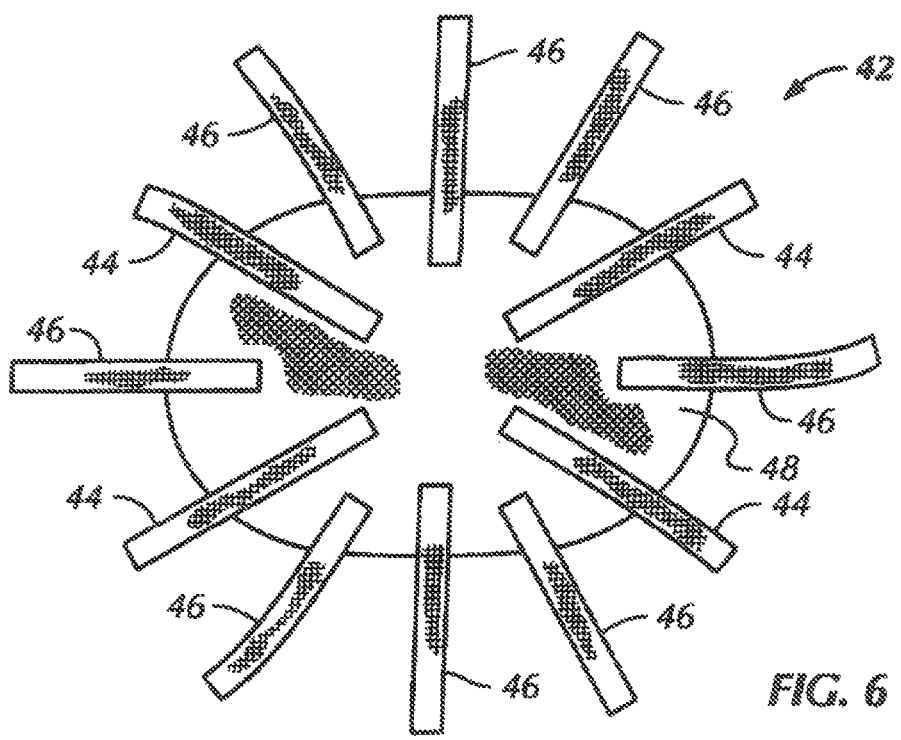
FIG. 6 is a plan view of an example mesh shown in FIGS. 2-5 suitably configured for ventral wall hernia repair, showing four centering straps and eight fixation straps.

Now addressing FIG. 6, a plan view of an example mesh implant such as the one shown in FIGS. 2-5 suitably configured for ventral wall hernia repair is shown. FIG. 6 shows, for non-limiting illustration, four centering straps 44 and eight fixation straps 46 attached to the mesh implant 42. It is to be understood that the centering straps 44 may be substantially similar in function and configuration to the centering straps 34 described above, while the fixation straps 46 in FIG. 6 may be substantially similar in function and configuration to the fixation straps 40 described earlier. Note that while FIG. 6 shows four straps 44 and eight straps 46, more or fewer straps may be used as desired.

Further, it may be appreciated from FIG. 6 that the body 48 of the implant 42 may be generally circular/radial in shape, though any other desired shape may be used to sufficiently cover a hernial opening such as, e.g. an oval. Still, it is noted that in FIG. 6, which shows the generally circular/radial implant 42, the centering straps 44 are attached to the implant 42 at radial locations that are less distanced from the center of the implant than where the fixation straps 46 are attached to the implant 42. It is to be understood that the straps 46 (and indeed the straps 44) are mounted inboard of the outer border of the body 48 such that when the implant 42 is positioned in its final intended position to cover a hernial defect, a protective margin of an antiadhesion layer in accordance with present principles prevents the abdominal viscera from contacting any portion of straps 46.

Figure 7:
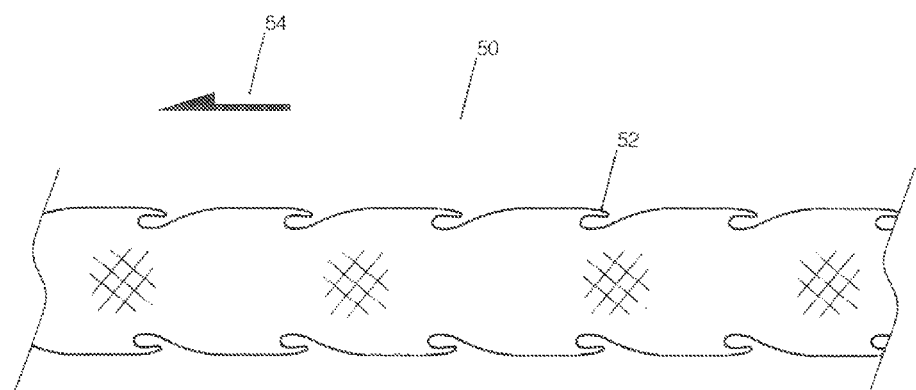
FIGS. 7 and 8 show alternate straps that are barbed to permit easy insertion of the straps into and optionally out of the patient but to impede withdrawal of the straps from the abdominal wall of a patient.
Figure 8:
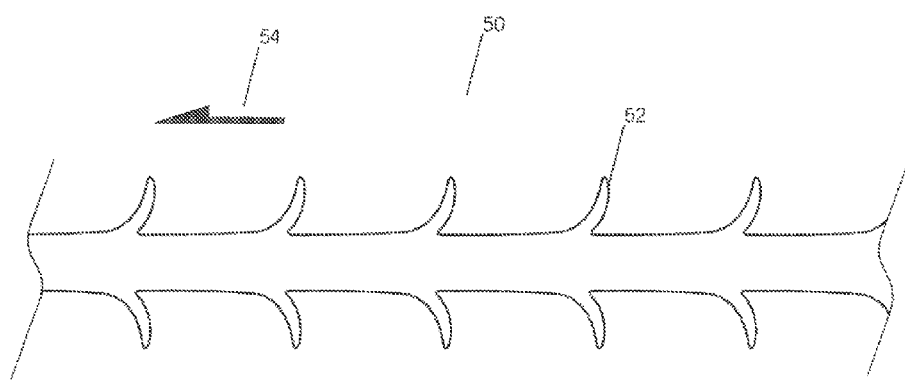

Referring to FIGS. 7 and 8, embodiments of one or more of the above-described centering and/or fixation straps are shown, generally designated 50, in which anchoring and/or adhesion spikes 52 are formed along one or both side edges of the strap 50 (FIG. 7) and/or along the flat face of the strap 50 that extends between the side edges (FIG. 8). The spikes 52 may be formed, e.g., by cutting the strap 50 and/or by using reinforced (molded) polypropylene. The spikes 52 as shown are equidistant from each other, but other spacings may also be used. The arrows 54 in FIGS. 7 and 8 indicate the direction of motion of the strap 50 being advanced into a patient to give perspective to the fact that the spikes 52 are barbed to permit easy movement of the strap 50 into the patient along the arrows 54 but to grip tissue when force is exerted on the strap 50 in a direction opposite the arrows 54.

Further describing the spikes 52, the strap 50 may define opposed thin edges and opposed flat surfaces extending between the edges such that at least one barbed spike extends from at least one edge and/or at least one flat surface. Only one spike may be included on the strap 50, or plural spikes 52 may be included on the strap 50 as shown in FIGS. 7 and 8. Additionally, note that the spikes 52 may be thin filaments oriented at oblique angles relative to a long axis of the strap 50. It may be appreciated that the long axis of the strap 50 is generally indicated by the arrows 54. However, the spikes 52 may be oriented at other angles depending on a specific implementation of the implant including the straps 50. Thus, e.g., the spikes 52 may be oriented perpendicular to a long axis of the strap 50 in some implementations.

Furthermore, the spikes 52 may be generally triangular to establish the barbed structure of the spikes 52 in some embodiments, but other shapes may be used in addition to or in lieu of the triangular structure such as, but not limited to, a double-barbed configuration established by two generally triangular structures jointly defining one spike 52. In essence, two triangular structures of a single "spike" are oriented at the same angle relative to the strap 52 and are connected to each other to establish a generally "M"-shape when the spike 52 is observed from a top-plane view in the double-barbed configuration. As an example of another exemplary configuration, a generally triangular spike may itself include relatively smaller spikes along respective edges thereof that are oriented at a similar angle as the larger spike relative to the strap 50.

In addition, note that any of the straps disclosed in the present application may have opposed thin edges that define a width of the strap. In some embodiments, the width may become progressively more narrow longitudinally along the strap from the end of the strap connected to the implant to a free end of the strap.

Figure 9:
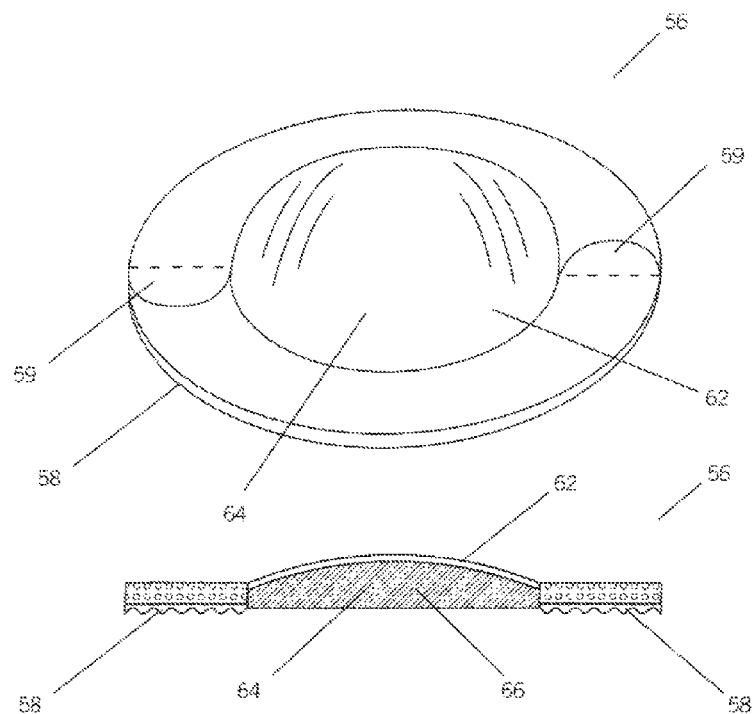
FIGS. 9 and 10 are perspective and partial cross-sectional views, respectively, of a skin seal through which strap retrieval tools and straps can be advanced without causing an undue loss of laparoscopic insufflation of the abdomen.
Figure 10:
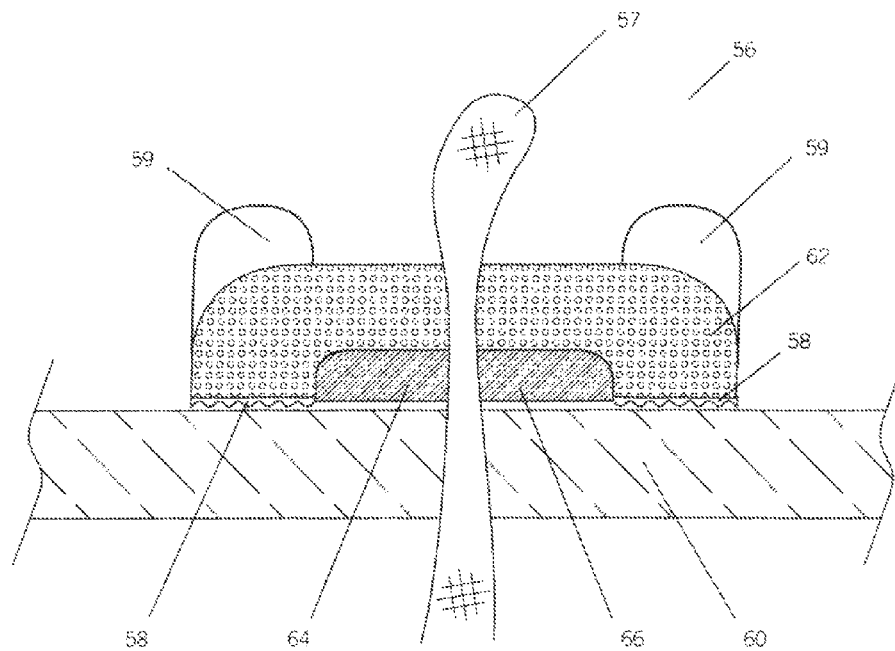

Now in cross-reference to FIGS. 9 and 10, a pneumatic seal 56 for laparoscopic surgery is shown in both perspective and partial cross-sectional views, respectively. Note that the seal 56 acts as a skin seal through which strap retrieval tools and straps such as the strap 57 shown in FIG. 10 can be advanced through, e.g., the abdominal wall of a patient without causing an undue loss of laparoscopic insufflation of the abdomen. Note that the pneumatic seal 56 may function not only as a seal for the strap 57 while being advanced out of the patient but also as a size marker, wound dressing, and/or skin lifter during hernia repair.

Regardless, the seal 56 includes a patient adhesion side 58 that is positionable against a patient's insufflated abdomen 60 to hold the seal 56 onto the patient. The adhesion side 58 may be made of an acrylic material in exemplary embodiments. The seal 56 also includes a puncture membrane 62 opposed to the patient adhesion side 58, which will be discussed further below.

Nonetheless, the seal 56 includes a sealant chamber 64 containing sealant 66 that is disposed under the puncture membrane 62, as may best be appreciated from FIG. 10. Thus, a piercing instrument (not shown) can be advanced through the puncture membrane 62 and sealant 66 in the sealant chamber 64 and into the patient's insufflated abdomen 60 such that the sealant 66 seals around the piercing instrument to impede leakage of insufflation gas from inside the patient's abdomen 60 along the piercing instrument to an area external to the patient. Thus, the sealant chamber 64 is under the puncture membrane 62 such that the puncture membrane 62 at least partially covers the sealant chamber 64 to thereby cause the sealant chamber 64 to be completely surrounded by the both puncture membrane 62 and adhesion side 58.

Furthermore, note that to aid a physician in advancing the piercing instrument and/or strap 57 through the seal 56 as described immediately above, gripping tabs 59 may be provided on the puncture membrane 62 or any other suitable portion of the seal 56 such that the tabs 59 may be gripped using a physician's hands and/or a surgical tool to facilitate advancement of the piercing instrument and/or strap 57 through the seal 56, and thus into the abdominal wall of the patient as shown. Also note that the tabs 59 may be foldable such that they may be easily folded against the puncture membrane 62 when desired as shown in FIG. 9 but still folded orthogonally away from the puncture membrane 62 as shown in FIG. 10 to facilitate gripping using, e.g., a surgical tool.

Also, it is to be understood that the puncture membrane 62 and/or sealant 66 may be made of high density closed cell foam, though other suitable materials may also be used. It is to be further understood that the sealant 66 may be made of a biocompatible substance including an antibiotic in exemplary embodiments. Even further, the sealant 66 may be made of a hydrogel, a biocompatible cream, grease, or jelly, and/or any combination of mixtures thereof.

Moving on, reference is now made to FIGS. 11-17. These figures schematically illustrate strap insertion tool advancement and strap retrieval steps of an example embodiment. Present principles recognize that a suitable hernial implant for any particular hernia repair may vary in size depending on, e.g., the size of the hernia sought to be repaired or the location of the hernia. As such, a physician may be required to determine what size implant should be used for a particular hernia repair as well as the position in which the implant should be placed prior to inserting the implant into the abdominal cavity of a patient.

Figure 11:
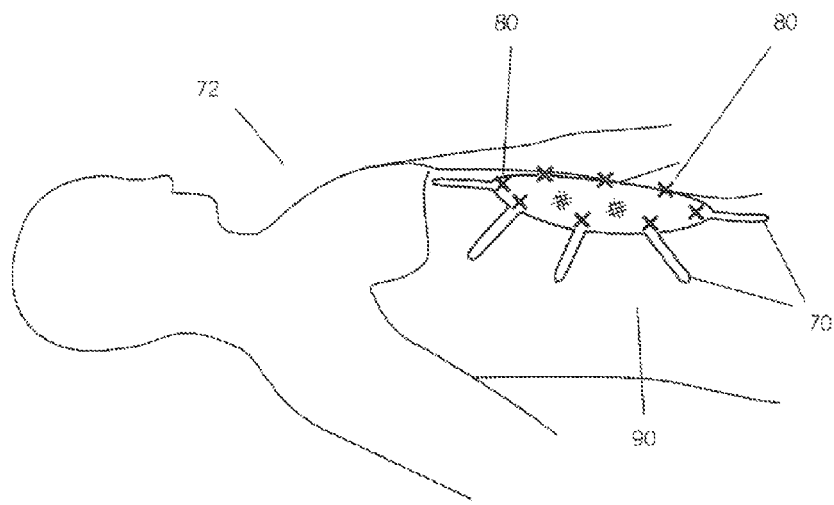
FIGS. 11-17 schematically illustrate strap insertion tool advancement and strap retrieval steps of an example embodiment.

Accordingly, as may be appreciated from FIG. 11, an implant 68 with plural straps 70 in accordance with present principles may be laid on top of a patient 72 to assist a physician in determining a proper implant size and position. However, present principles also recognize that instead of laying the implant 68 on top of the patient 72, a pattern and/or template of the implant may instead be laid atop the abdomen of the patient 72 so that, e.g., the implant 68 is not exposed to elements that would otherwise render the implant 68 non-sterile and/or no longer useful for hernial repair.

Regardless, as may be appreciated from FIG. 11, the implant 68 (or alternatively, a pattern of the implant) is laid on top of the abdomen 90 of the patient 72 to cover a hernia (not shown). A physician may indicate on the exterior surface of the abdomen 90 a strap end retrieval piercing location 80 for at least some ends of respective straps 70. If desired, to facilitate proper placement of the implant 68 (or alternatively a pattern) to ensure proper marking of the location 80, an abdominal space inside the patient may be illuminated such that light from the space propagates through the patient's abdominal wall layers to give a visual indication outside the patient of interior tissue of the patient including blood vessels to thus facilitate appropriate marking of the location 80. Visual indication of, e.g., blood vessels allows a physician to perform strap retrieval/insertion through the abdominal wall without transecting the vessels.

A physician may then advance the implant 68 into the insufflated abdomen of the patient 72 through a trocar and unfold the implant inside the patient 72. The physician may thus use the piercing locations 80 indicated on the abdomen of the patient 72 to retrieve straps 70 up into the patient's tissue by advancing a snaring instrument into the patient 72 through one of the piercing locations 80. The end of a strap 70 is then snared and the strap may then be pulled outwardly away from the patient's abdominal cavity.

Furthermore, if desired the straps 70 may have different colors on respective portions thereof and the marking locations may be respectively colored to correspond to the different colors of the straps 70 such that a physician may discern which strap should be advanced through a particular marking location. Put another way, a color code may be established wherein each respective strap and its corresponding marking location have substantially the same color such that they are distinguishable over other straps and marking locations to provide a color-coding means by which a physician may associate each one of the straps 70 with a particular piercing location for the strap. Furthermore, if desired, none of the straps and marking locations may have the same color from the color code as any other respective strap or marking location.

Alternatively or in addition to the color-coding described above, each strap may be marked, notched, folded, etc., differently from the other straps on at least respective portions thereof to distinguish them from each other and further assist a physician when retrieving the straps 70 through the piercing locations 80 to, e.g., prevent crossover or sequencing errors. Note that in some embodiments the marking may be defined by a structural difference and/or visual difference on the strap relative to the other straps.

Figure 12:
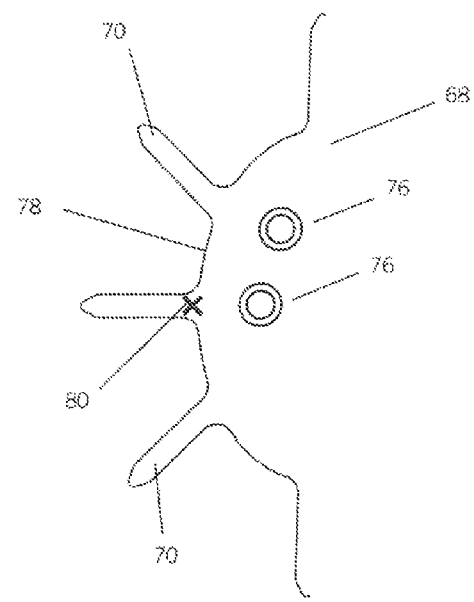

Regardless of the foregoing discussion on strap color-coding and/or marking, in exemplary embodiments the step of indicating on the abdomen of a patient 72 a strap end retrieval piercing location 80 may also include disposing a pneumatic seal 76 (such as the one described above) on the abdomen of the patient 72 to help determine the piercing location 80, as illustrated by FIG. 12. Thus, it may be appreciated from FIG. 12 that the pneumatic seal 76 may be positioned on the patient 72, e.g., three to five centimeters inboard of the periphery 78 of the implant 68 such that it may, e.g., accommodate tunneling length. As shown in both FIGS. 11 and 12, note that an "X" denotes the piercing location 80. Also note that the piercing location 80 may be indicated using any suitable ink such as surgical ink.

Regardless, the seal 76 is positioned inboard of the periphery 78 to assist a physician in properly marking the piercing location 80. More specifically, the seal 76 gives a physician a frame of reference for the lateral distance in a patient's abdominal wall through which the strap 70 will be advanced before being advanced toward the exterior of the patient's abdominal wall after entering the abdominal wall from the patient's abdominal cavity orthogonal to the piercing location 80. Thus, placing the seal 76 inboard of the periphery 78 facilitates proper marking of the piercing location. However, note that in other implementations the seal 76 may be placed outboard of the periphery 78 such that the strap 70 may be advanced through the abdominal wall laterally away from the body of the implant 68. Either way, it is to be understood that the seal 76 may be positioned closer or farther away from the periphery 78 as desired.

Figure 13:
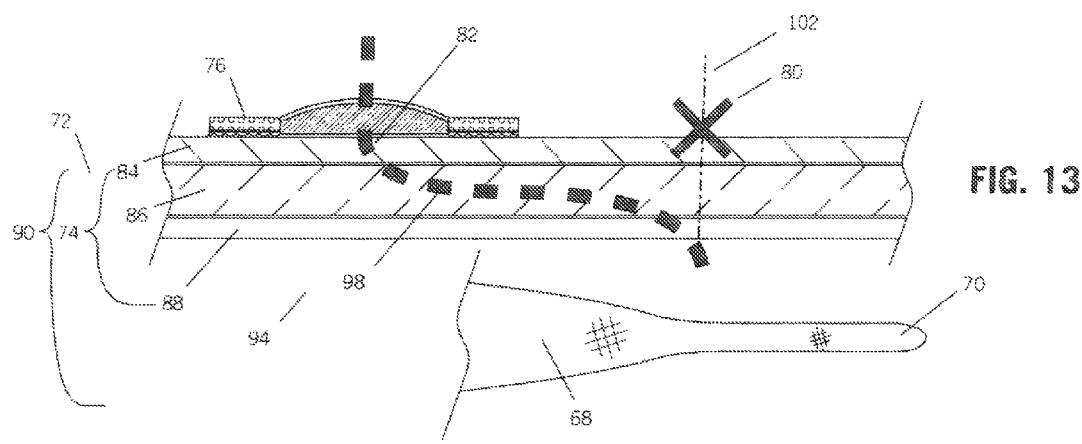

Moving on to FIG. 13, it may be further appreciated that the pneumatic seal 76 is positioned external to the skin and/or abdominal wall of a patient. More specifically, the pneumatic seal 76 is positioned external to a skin/fat/fascia layer 84 (referred to herein' as the "skin layer" 84 for convenience). It may also be appreciated that the abdominal wall 74 includes a muscle layer 86 and peritoneum layer 88. Note that the layers 84, 86, and 88 at least partially define the abdominal wall 74. It may also be appreciated from FIG. 13 that the seal 76 is not positioned directly over the strap end retrieval piercing location 80 but rather distanced from it as set forth herein. Further, FIG. 13 also shows that the hernial implant 68 is already advanced into the abdominal cavity 94 of the patient 72.

As indicated above, the seal 76 is not positioned directly over the piercing location 80 but rather is positioned laterally distanced from the location 80. It may be appreciated that a curved retraction path/channel 98 to retract an end of a strap 70 may be established by, e.g., a physician as described further below. Accordingly, note that the path 98 may be curved and is formed through tissue of the patient 72 (such as the layers 84, 86, and 88) by advancing a curved piercing instrument through the layers 84, 86, and 88 to establish the path 98.

With more specificity, the piercing instrument may be advanced into the patient 72 from a location external to the skin layer 84 and inboard of the piecing location 80, such as the location 82 under the pneumatic seal 76, to establish the curved retraction path 98. Note that the piercing instrument may first be advanced through the seal 76 to impede leakage of insufflation gas front inside the patient's abdomen 90 prior to being advanced into the skin layer 84 and hence into the abdominal wall 74. Put another way, the piercing instrument is passed through the seal 76, tunneled through the skin layer 84, tunneled through the subcutaneous tissue, tunneled outwardly and/or laterally through the abdominal rectus muscles, and then exits through the peritoneum layer 88 into the abdominal cavity 94 at a location parallel to an anterior-posterior dimension defined by the body of the patient 72, and indeed a location substantially posterior (e.g., under) to the piercing location 80 as indicated by the axis 102. Thereafter, a snaring instrument may be advanced into the patient along the curved path 98 to retrieve an end of the strap 70 inside the abdominal cavity 94.

Note that to facilitate advancing the piercing and snaring instruments into the patient 72, the abdominal cavity/space 94 may be illuminated in accordance with present principles such that light from, e.g., the cavity 94 propagates through the skin layer 84 to give visual indication outside the patient 72 of interior tissue of the patient including blood vessels to thereby facilitate advancing of the piercing and snaring instruments into the patient 72. It may now be appreciated from FIG. 13 that the path 98 is a path for the strap 70 of the implant 68 to be advanced through as shown in FIG. 14, preferably under illuminated conditions, such that the strap 70 enters the peritoneum layer 88 from inside the abdominal cavity 94 at a location at least substantially posterior to the piercing location 80 and is advanced at least partially laterally through the path 98 toward the skin layer 84 using a snaring instrument.

Figure 14:
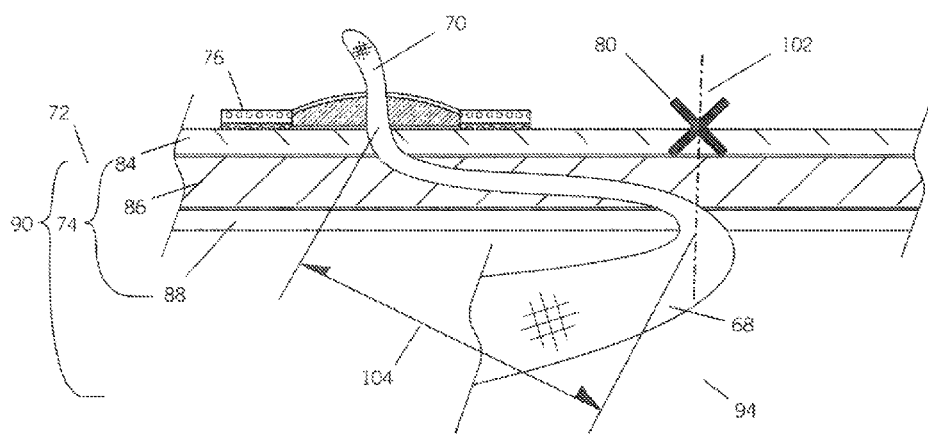

Accordingly, to facilitate strap engagement/securement with the abdominal wall 74 of the patient 72 by way of friction in accordance with present principles to, e.g., minimize patient discomfort while still ensuring that the implant 68 remains in its intended position/orientation when so placed, it may be further appreciated from FIG. 14 that after the strap 70 has been snared in the abdominal cavity 94 by a snaring instrument, the strap 70 is advanced into the peritoneum layer 88 from inside the abdominal cavity 94 when guided by the snaring instrument. The snaring instrument may thus advance the strap 70 at least somewhat laterally through the muscle layer 86 through the path 98 as shown in FIG. 14. After being advanced laterally through the muscle layer 86, the strap 70 is then passed through the skin layer 84 and through the pneumatic seal 76 to impede leakage of insufflation gas from the abdominal cavity 94, as may also be appreciated from FIG. 14.

To reiterate, it may be appreciated from FIGS. 13 and 14 that the pneumatic seal 76 through which the strap 70 is to be passed is laterally distanced from the piecing location 80. Thus, after an end of the strap 70 is pulled at least partially through the skin layer 84 and through the seal 76, and hence pulled away from the abdominal cavity 94, the strap 70 still at least partially resides in a lateral orientation along the path 98 relative to the anterior-posterior dimension defined by the body of the patient 72.

Furthermore, it may be appreciated that by advancing the strap 70 laterally through the muscle layer 86 relative to an anterior-posterior dimension defined by the body of the patient 72 using, e.g., a snaring instrument (as opposed to advancing the strap 70 more centrally along a path parallel to the anterior-posterior dimension such as, e.g., along the axis 102), friction between the abdominal wall 74 of the patient 72 and the strap 70 is increased even further (and further still if spikes such as the ones described above are included on the strap 70). However, the use of friction rather than, e.g., sutures, nonetheless provides a relatively more tension-free condition between the strap 70 and abdominal wall 74 while still securing and stabilizing the implant 68.

Also, note that if desired the end of the strap 70 may be pulled through the seal 76 and completely out of the patient as shown in FIG. 14, though it is to be understood that the end of the soap 70 may instead be pulled outwardly yet still allowed to reside in subcutaneous tissue such as, e.g., the muscle layer 86, without pulling the strap end all the way out of the patient 72. Additionally, note that even should the end of the strap 70 be pulled completely out of the patient 72, the abdomen 90 of the patient 72 may then be tented as described below to cause the end of the strap 70 to slip below the surface of the skin layer 84 such that the end of the trap 70 is thereafter allowed to reside in subcutaneous tissue of the patient 72.

Regardless, an increased area of friction between the strap 70 and layers 84, 86, and 88 of the patient 72 may be appreciated from the arrows 104 of FIG. 14. It may also be appreciated that the increased area of friction indicated by the arrows 104 (and thus increased friction between the strap 70 and abdominal wall 74 of the patient 72) created by advancing the strap 70 laterally through the layer 86 is relatively larger than if the strap 70 were instead only advanced centrally through an anterior-posterior dimension defined by the body of the patient 72, such as along the axis 102.

Even further, due to intra-abdominal pneumoperitoneum pressure, note that tissue around the mesh strap 70 may be tightened and/or squeezed and thus further impede leakage of insufflation gas from inside the patient's abdomen 90. Also note that the seal 76 conforms so the mesh structure of the strap 70 when the strap 70 is advanced therethrough, which further impedes leakage of insufflation gas. The tissue compression around the strap may in some instances minimize or eliminate the need for a pneumatic seal, hut the remaining structures and methods described herein are understood to nonetheless apply even if a physician determines that a seal need not be used. Furthermore, note that if a seal is to not be used in certain instances, a surgical clamp such as, e.g., a bulldog, may be used to clamp the skin around the strap end until trimming and surgical skin closure is accomplished in accordance with present principles.

Figure 15:
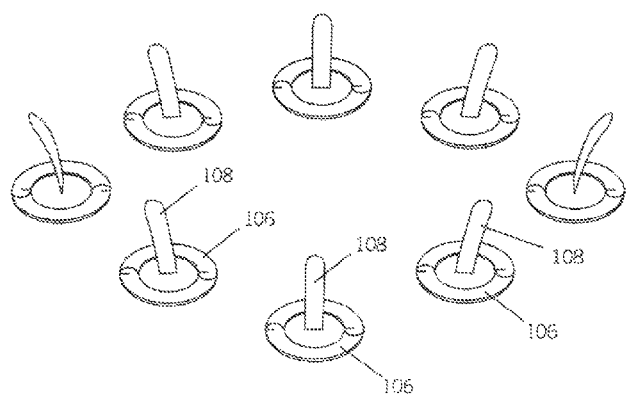

Now in reference to FIG. 15, it may be appreciated that plural pneumatic seals 106 are shown on a patient's abdomen 110 with plural ends of straps 108 advanced from the abdomen 110 through the seals 106. It is to be understood that the straps 108 have been advanced through the abdomen 110 and seals 106 as set forth in reference to FIGS. 11-14. Note that subsequent adjustment of an implant's position may be performed incrementally as each end of a strap is advanced through a respective seal 106, or a "final" adjustment may be performed, after all ends of straps 108 have been advanced through their respective seals 106 as shown in FIG. 15. However, it is to be understood that still other adjustment after the "final" adjustment may nonetheless be made as needed.

Figure 16:
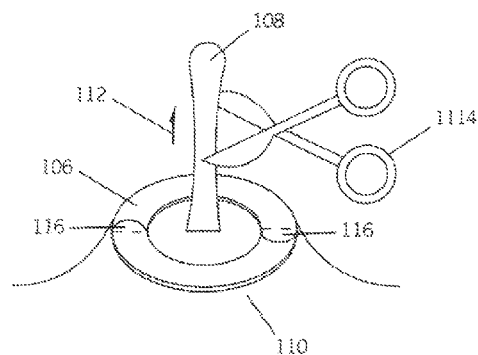

As may be better appreciated from FIG. 16, a strap 108 is pulled externally away from the abdomen 110 as indicated by arrow 112 to thereby adjust an implant (not shown) having the strap 108. An adjustment may be made to, e.g., position the implant up against the inside of the abdominal wall as closely as possible to a patient's hernia such that there is little or no space between the implant and hernial area. This adjustment may be made using a surgical tool, or the physician may do so simply by using his or her hands. Scissors 114 or any other suitable cutter or surgical instrument may then be used to cut off and/or remove excess material from the strap 108.

Figure 17:
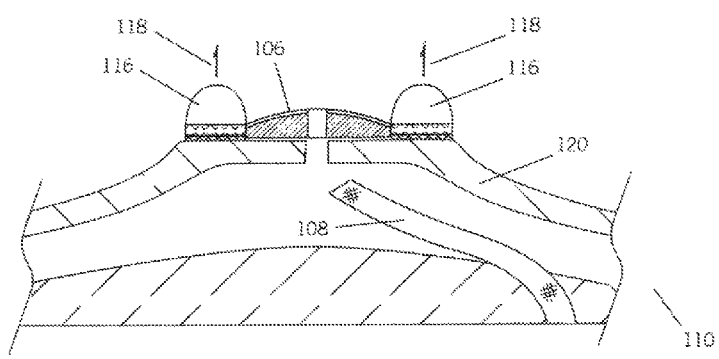

Then, as shown best in FIG. 17, gripping tabs 116 on the seal 106 substantially similar in configuration to the gripping tabs 59 described above may be pulled away from the skin 120 of a patient by a physician using his or her hands or alternatively using a surgical tool, as indicated by arrows 118. The force pulling the seal 106 away from the skin 120 thus causes the now trimmed/cut strap 108 to be positioned subcutaneously. This occurs at least partially due to a tenting of the skin 120, as shown in FIG. 17, caused by the force pulling the seal 106 away from the skin 120. After the "final" adjustment described in reference to FIG. 15-17, the seal 106 may be left as a dressing after hernia repair surgery, or it may be removed so that a more conventional dressing may be applied subsequent to surgery.

Figure 18:
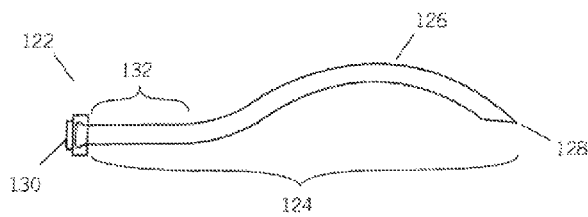
FIG. 18 shows a guide wire introducer tool configured for effecting a lateral (relative to the anterior-posterior dimension) strap channel in the patient.

Turning now to FIG. 18, a guide wire introducer tool configured for effecting a lateral (relative to the anterior-posterior dimension) strap channel/path in the patient is shown. Accordingly, a guide wire introducer tool 122 includes a hollow tube assembly 124 defining a curved distal end segment 126 terminating at an open distal end 128. The assembly 124 may be made of metal in exemplary embodiments. The curved distal end segment 126 directs the open distal end 128 through abdominal wall tissue to establish a channel/path such as the path 98 described above under manipulation of, e.g., a physician. The curved distal end segment 126 may be of any suitable degree of curvature.

The tool 122 also includes a septum seal 130 to prevent gas loss in accordance with present principles. Note that, if desired, the assembly 124 may include a substantially straight proximal end segment 132 between the curved distal end segment 126 and septum seal 130. If desired, the proximal end segment 132 may extend into the septum seal 130, or alternatively the septum seal 130 may attach to the end of the proximal end segment 132 distanced from the distal end segment 126. It may be appreciated that owning at least in part to the curved distal end segment 126, the open distal end 128 may be relatively easily rotated to exit an abdominal wall of a patient and enter the patient's abdominal cavity.

Furthermore, note that the open distal end 128 is understood to be sharp enough to puncture the skin of a patient and then establish a guide wire path/channel such that a strap may then be advanced through path/channel in accordance with present principles. Also note that a laparoscope may be used for illumination such that light from inside the abdominal cavity propagates through the patient's skin to give visual indication outside the patient of interior tissue of the patient to assist a physician in avoiding blood vessels when advancing the tool 122 through the abdominal wall of a patient.

It is to be understood that a guide wire may then be inserted through the tool 122 including assembly 124 and then the tool 122 may be removed from the patient, leaving the guide wire in place such that it extends from outside the abdominal wall of a patient, through the channel/path established by the tool 122, and into the abdominal cavity. Thereafter, a strap passer may be introduced over the guide wire in accordance with the principle set forth below. In this way, a channel/path as described above may be established and a guide wire may be advanced therethrough, as set forth more specifically below.

Thus, in cross-reference to FIGS. 19-23, these figures illustrate a strap retrieval tool that can be advanced over a guide wire, it being understood that the guide wire was inserted by means of, e.g., the guide wire introducer tool 122 of FIG. 18. Accordingly, the tool described in reference to FIGS. 19-23 may be referred to as a transcutaneous "strap-passer" that uses an over-wire style.

Regardless, FIGS. 19-23 show various operational configurations to retrieve a strap in accordance with present principles. Accordingly, a snaring instrument 134 for snaring a strap of a hernia repair implant disposed in a patient's abdomen such as those described above includes an elongated tube assembly 136. The assembly 136 defines a distal end segment 138 that may be tapered and/or dilating in some embodiments. The distal end segment terminates at an open distal end 140. The assembly 136 also includes a guide wire opening 142 in the distal end segment 138 for receiving a guide wire 144 therethrough such that the distal end segment 138 can ride along the guide wire 144 extending through the open distal end 138 and guide wire opening 140.

However, note that in other embodiments the guide wire 144 may be received by a proximal segment 146 and extend at least partially through the proximal segment 146, entirely through the distal segment 138, and thus exit the guide wire opening 140 such that both the segments 138 and 146 can ride along the guide wire 144. Regardless, as shown in FIGS. 19-23, the snaring instrument 134 is understood to be inside the abdominal cavity of a hernia repair patient such that it may retrieve a centering or fixation strap after the instrument 134 is advanced into the abdominal cavity of a patient through a channel/path using the guide wire 144.

Additionally, note that once the snaring instrument 134 is advanced through the desired channel/path and into the abdominal cavity of the patient at least in part using the guide wire 144, the guide wire 144 may be withdrawn from the instrument 134 and advanced back through the channel/path and out of the patient since, in exemplary embodiments, the instrument 134 may itself be advanced back through the channel/path once a strap has been snared without assistance of the guide wire. This may be appreciated from FIGS. 22 and 23, still showing the instrument 134 in the abdominal cavity but not showing the guide wire 144.

Figure 19:
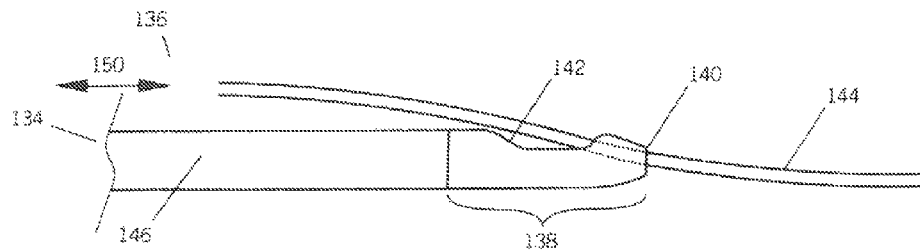
FIGS. 19-23 illustrate a strap retrieval tool that can be advanced over the wire inserted by means of the guide wire introducer tool of FIG. 18, in various operational configurations to retrieve a strap.
Figure 20:
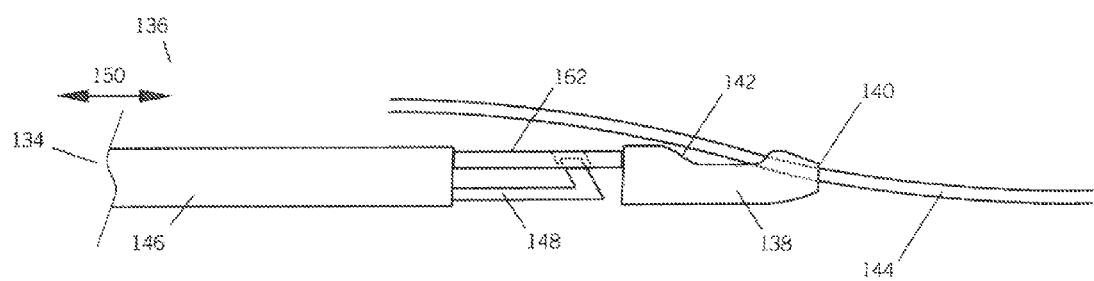
Figure 21:
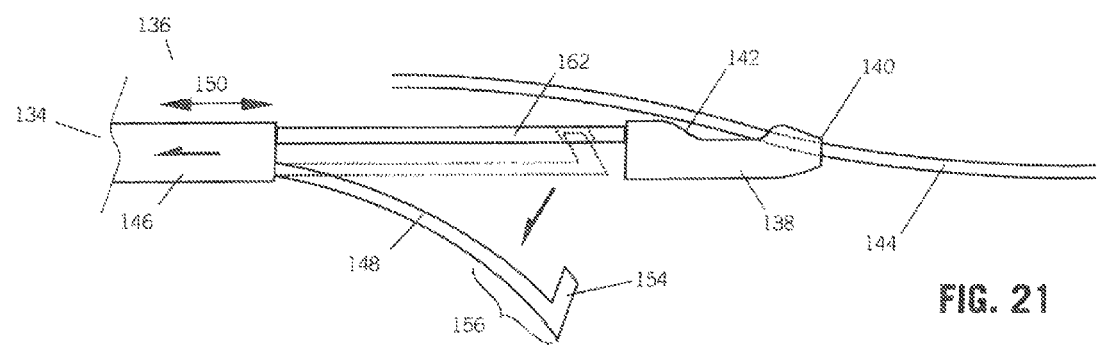

For completeness, note that the tube assembly 136 of FIGS. 19-23 also defines the proximal segment 146 and a connecting segment 162 between the distal segment 138 and proximal segment 146. As may be appreciated by comparing FIG. 19 with FIGS. 20-23, the segments 138 and 146 are movable relative to each other between a juxtaposed configuration as shown in FIG. 19 in which the proximal segment 146 is closely juxtaposed with the distal segment 138, and a separated configuration as shown in FIGS. 20-23 in which the proximal segment 146 is distanced the distal segment 138 yet still mechanically connected thereto at least partially due to, e.g., the connecting segment 162. FIG. 20 thus shows the segments 138 and 146 as they are being transitioned into the separated configuration, and FIG. 21 shows the segments 138 and 146 substantially positioned into the separated configuration.

Furthermore, a movable grasping jaw 148 is shown in FIGS. 20-23. The jaw 148 is understood be within the assembly 136 as shown in FIG. 19 but is not shown in that figure since the assembly 136 is in the juxtaposed position. Thus, the grasping jaw 148, while the assembly 136 is in the juxtaposed configuration, is understood to be oriented longitudinally within the assembly 136. This may indeed be appreciated from FIG. 20, where the segments 138 and 146 are being moved from the juxtaposed configuration to the separated configuration and the jaw 148 is still at least somewhat oriented longitudinally within the assembly 136. Regardless, it is to be understood that the jaw 148 is used to grasp a strap 152 so that the strap 152 may be advanced with the instrument 134 through a channel/path toward an anterior portion of the patient's abdominal wall. Grasping the strap 152 with the grasping jaw 148 in accordance with present principles may best be appreciated from FIGS. 22 and 23.

Note that in some embodiments, the grasping jaw 148 may have more than one tooth and the teeth may be located longitudinally along the grasping jaw 148. Further still, the teeth may be equidistant from each other if desired. However, as may be appreciated from FIG. 21, a single tooth 154 is shown in the present embodiment. The tooth 154 is located at a distal end 156 of the grasping jaw 148 and may extend substantially orthogonally away from to a distal end 156 toward the distal segment 138. Additionally, the tooth 154 may be generally triangular, as may also be appreciated from FIG. 21. Nonetheless, it is to be understood that the tooth 154 may instead extend at an oblique angle away from the distal end 156 in other embodiments, if desired.

Furthermore, note that in exemplary embodiments, when the assembly 136 is in the separated configuration show in, e.g., FIG. 21, the proximal segment 146 is distanced from the distal segment 138 to permit the movable grasping jaw 148 to assume, under material bias (or alternatively/additionally, under spring bias), a grasping position to grasp at least part of a lateral segment of the strap 152. Moreover, note that a separate element not shown, such as a wire, rod, or string, may be disposed within the proximal segment 146 and attached to an end of the jaw 148 disposed within the segment 146 (i.e. opposite the end having the tooth 154) to facilitate manipulation the jaw 148 to move it from the relatively open grasping position back toward a closed position and vice versa. Note that the closed position of the jaw 148 after grasping the strap 152 may best be appreciated best from FIG. 23.

Figure 22:
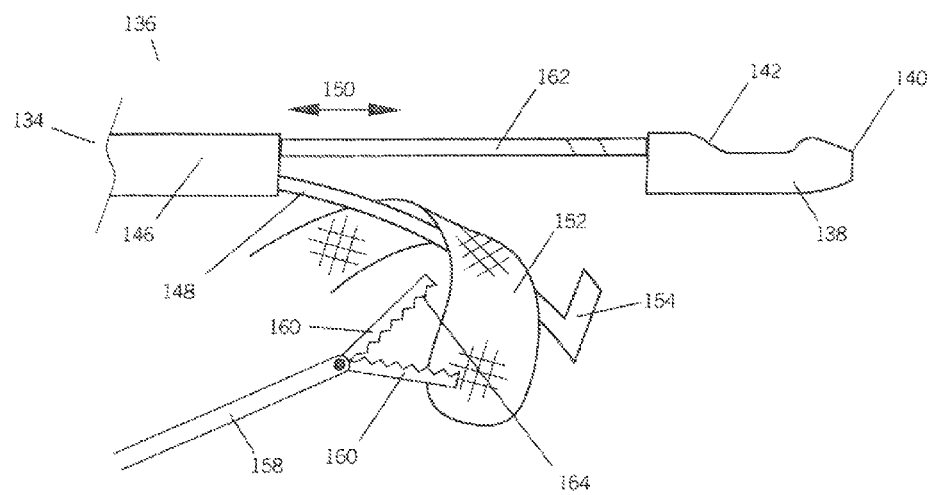
Figure 23:
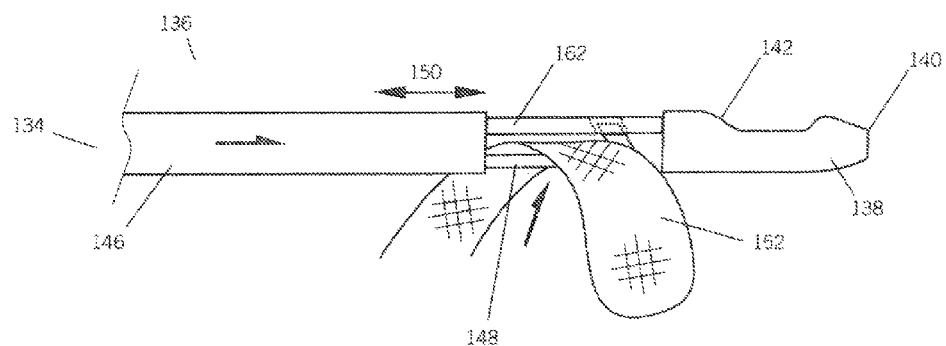

Momentarily reverting back to FIG. 21, it is to be understood that when in the grasping position, the grasping jaw 148 is oriented at an oblique angle relative to a long axis 150 defined by the assembly, and a free distal end of the jaw 148 is disposed radially outward of the segments 138 and 146. Accordingly, the strap 152 can be positioned between the jaw 148 and connecting segment 162, as shown in FIG. 22. The assembly 136 can then be moved back substantially to the juxtaposed configuration to trap the strap 152 for retrieval, as shown in FIG. 23.

Notwithstanding the foregoing, it is to be understood that the strap 152 may prevent the assembly 136 from being moved back completely to the juxtaposed configuration in some embodiments due to an area within the assembly 136 being occupied by the strap 152. Whether or not the assembly 136 is moved completely back to the juxtaposed configuration may indeed be dependent on the dimensions of the strap 152. Nonetheless, note that either way the assembly 136 is moved back substantially to the juxtaposed configuration such that it is no longer in the separated configuration.

It may now be appreciated that the snaring instrument 134 may be used to snare a strap so that the strap may then be advanced from the abdominal cavity of a patient through a channel/path, where the channel/path has at least one portion extending laterally through the patient's abdominal wall in accordance with present principles. Furthermore, if desired a surgical tool 158 having a grasping distal end 160 (as shown best in FIG. 22) including opposing grasping edges 164 with teeth may be used by a physician to move the strap 152 toward the instrument 134 so that the jaw 148 may more easily receive the strap 152.

Figure 24:
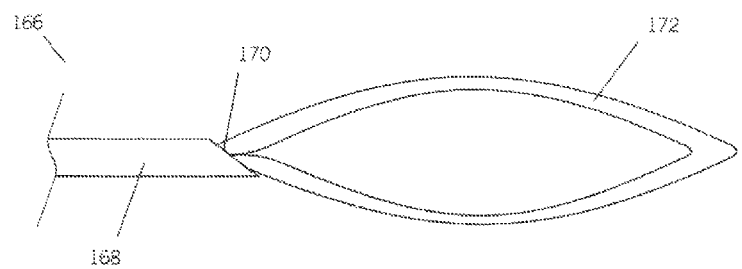
FIG. 24 is a schematic view of a first strap retrieval element that can be used in the strap retrieval tool of FIGS. 19-23.

Moving on to FIG. 24, a schematic view of a strap retrieval element that can be used in the strap retrieval tool of FIGS. 19-23 is shown. Thus, rather than using the grasping jaw 148 described above, an elongated tube assembly 166 defining a distal end segment 168 terminating in an open distal end 170 includes a loop 172 extending out of the open distal end 170. In exemplary embodiments, the loop 172 is made of nitinol, though other suitable materials may be used. Note that the loop 172 is shown in an extended position in FIG. 24. It may thus grasp a strap, such as the centering and fixation straps discussed above, by receiving an end of the strap through the loop 172 and using friction to advance the strap out of the patient's abdomen. Alternatively, the loop 172 may be at least partially retracted into the elongated tube assembly 166 such that the loop 172 shrinks, cinches, and/or closes around the strap to grip it. When retracted, it is noted that at least pan of the loop 172 is oriented longitudinally within the elongated tube assembly 166.

Furthermore, though not shown in FIG. 24, a separate element such as a wire, rod, or string may be disposed within the assembly 166 and attached to the end of the loop 172 (or alternatively may define the end portion of the loop 172)

closest to the distal segment 168 to facilitate extension and retraction of the loop 172 to move it from the relatively extended position shown to a relatively retracted position. It may now be appreciated that FIG. 24 provides yet another instrument for grasping a strap and hence facilitating strap retrieval.

Figure 25:
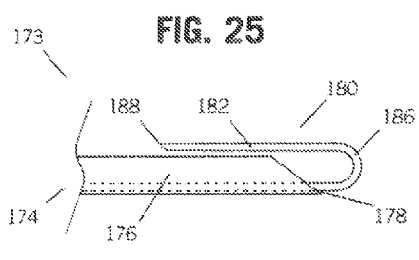
FIGS. 25 and 26 are schematic views of a second strap retrieval element that can be used in the strap retrieval tool of FIGS. 19-23.
Figure 26:
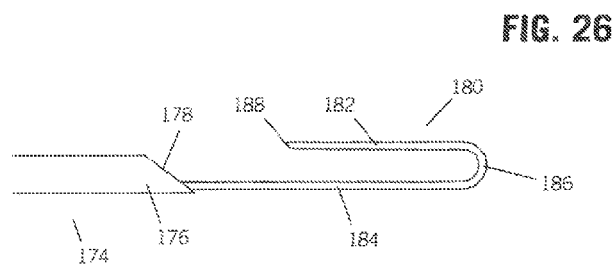

Turning now to FIGS. 23 and 26, schematic views of another strap retrieval element that can be used in the strap retrieval tool of FIGS. 19-23 are shown. Thus, a snaring instrument 173 for snaring a strap of a hernia repair implant disposed in a patient's abdomen in accordance with present principles includes an elongated tube assembly 174 defining a distal end segment 176 terminating at an open distal end 178. Differing from the embodiments discussed above, FIGS. 25 and 26 show a curved hook member 180 pushable out of the distal end 178.

It is to be understood that the curved hook member 180 has a first leg 182 and a second leg 184 that are co-parallel to each other and are joined together by a curved distal high 186. The first leg 182 terminates at a proximal end 188 thereof. Thus, the hook member 180 is movable between an extended position, as shown in FIG. 26, and a retracted position, as shown in FIG. 25. In the extended position shown in FIG. 26, the proximal end 188 is exposed such that a strap can be passed proximal to the proximal end 188 of the first leg 182 to dispose the strap between the legs 182 and 184. In the retracted position shown in FIG. 25, the proximal end 188 of the first leg 182 is not exposed to thereby trap the strap between the legs 182 and 184 for retrieval. Note that, when in the retracted position, the proximal end 188 may either terminal at the open distal end 178 or may advance at least partially through the open distal end 178 into the a distal end segment 176 as desired to, e.g., advance the instrument 173 into and out of a patient with greater ease.

In other words, in exemplary embodiments the assembly 174 may be advanced through a channel/path in the retracted position of FIG. 25. It can then be placed in the extended position of FIG. 26 while at least partially in the patient's abdomen by pushing on the leg 184, where the leg 184 is understood to extend into the assembly 174, to place the assembly 174 in a configuration to grasp a strap. Once a strap has been passed proximal to the proximal end 188 and is between the legs 182 and 184, the leg 184 may be pulled to return the assembly 174 to the retracted position, this time with the strap trapped in the curved hook member 180 at least partially due to the curved distal bight 186 enclosing the strap. Note that another element such as a wire or rod may be attached to the leg 184 inside the distal segment 176 to help perform the pushing and pulling disclosed above and facilitate strap retrieval.

Figure 27:
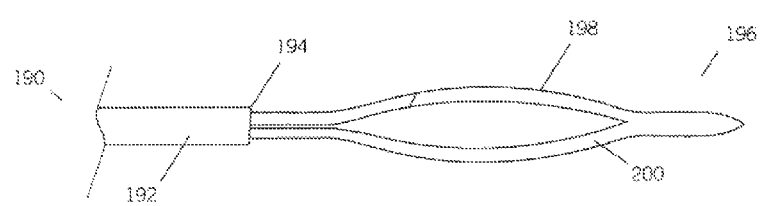
FIGS. 27 and 28 are schematic views of a third strap retrieval element that can be used in the strap retrieval tool of FIGS. 19-23.
Figure 28:
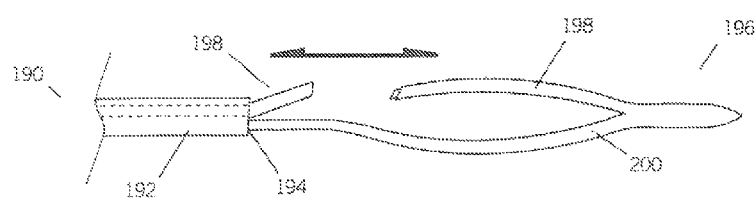

Now in cross-reference to FIGS. 27 and 28, schematic views of yet another strap retrieval element that can be used in the strap retrieval tool of FIGS. 19-23 are shown. Accordingly, a snaring instrument for snaring a strap of a hernia repair implant disposed in a patient's abdomen includes an elongated tube assembly 190 defining a distal end segment 192 terminating at an open distal end 194. The assembly 190 also includes a snare member 196 extending out of the distal end 194. It is to be understood that the snare member 196 has a first leg 198 and a second leg 200.

Furthermore, note that the first leg 198 is movable between a closed configuration, as shown in FIG. 27, and an open configuration, as shown in FIG. 28. When the assembly 190 is in the closed configuration, the legs 198 and 200 form a completely enclosed loop. If desired, the assembly may be advanced through a channel/path and into a patient's abdominal cavity in a retracted configuration such that the snare member 196 is retracted partially or completely within distal segment 192 in accordance with present principles. Regardless, when the assembly 190 is in the open configuration as shown in FIG. 28, a gap is established through the first leg to permit a strap to pass therethrough. The assembly 190 may then be returned to the closed configuration shown in FIG. 27 to trap a strap to be retrieved. Again note that, e.g., one or more wires of rods may be used in accordance with present principles to facilitate the transition from the closed configuration to the open configuration, and vice versa.

Figure 29:
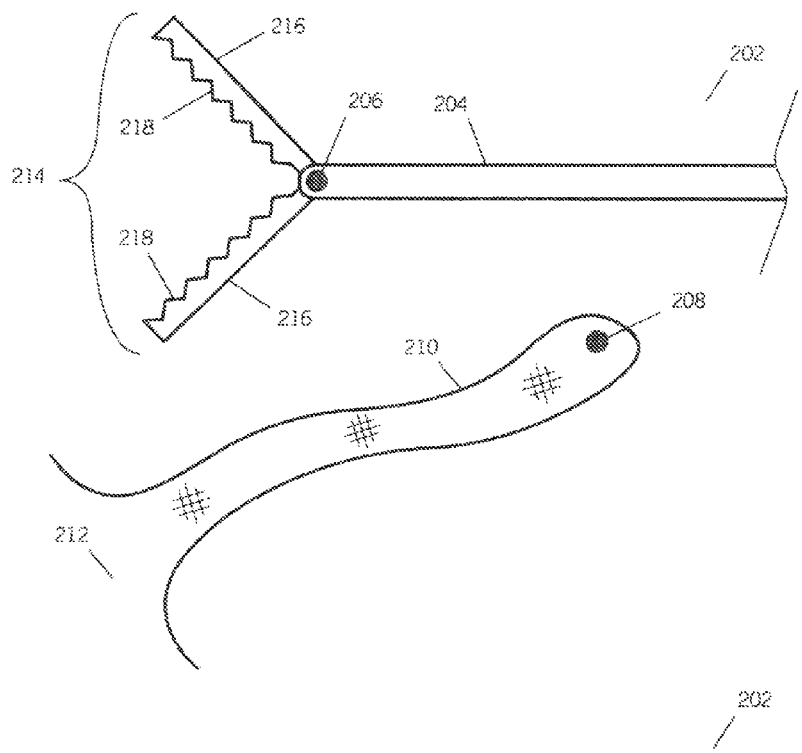
FIGS. 29 and 30 are schematic views of a fourth strap retrieval element that can be used in the strap retrieval tool of FIGS. 19-23.
Figure 30:
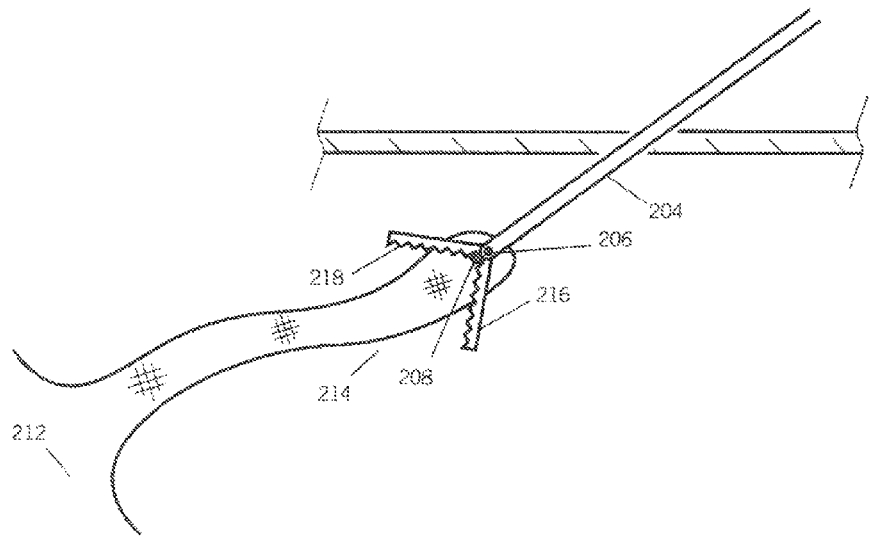

Moving on, reference is now made to FIGS. 29 and 30, which are schematic views of another snaring element that can be used m the strap retrieval tool of FIGS. 19-23. Thus, a snaring instrument for snaring a strap of a hernia repair implant disposed in a patient's abdomen includes an elongated tube assembly 202 defining a distal end segment 204. FIGS. 29 and 30 also show a magnet 206 disposed on the distal segment 204 to attract a magnet 208 on a strap 210 of a hernial implant 212. Even further, a grasping member 214 is located on the distal end segment 204 and is understood to be movable between an open position and a closed position to grasp and then hold the strap 210. It is to be understood that in some exemplary embodiments, the magnetic properties of the magnet 206 on the assembly 202 may be operator-controlled using electromagnetics understood by those within the art such that only an intended strap of an implant having plural straps may be isolated and/or captured using magnetism when desired.

As may be appreciated front FIG. 29, in exemplary embodiments the grasping member 214 has opposing grasping blades 216 extending orthogonally away from the distal segment 204. The grasping blades 216 have plural teeth 218 as shown, though it is to be understood that each blade 216 may only have one tooth if desired. If only one tooth is used, the tooth may be located at or near a distal end of the grasping blade 216 relative to the assembly 202, though not required.

Moreover, note that while the teeth 218 at least somewhat resemble triangular geometric figures, in other embodiments or in addition to the triangular teeth 218, still other shapes for the teeth 218 may be used, such as generally rectangular teeth and/or hooks. Regardless, it may be appreciated from FIGS. 29 and 30 that strap retrieval is facilitated both due to the ability of grasping member 214 to grasp the strap 210 and due to the attraction of the magnets 206 and 208 to more easily guide the strap 210 between the opposing blades 216 of the grasping member 214. The strap may then continue to be grasped as it is advanced through a channel/path toward an anterior surface of the patient's abdomen in accordance with present principles.

Now cross-referencing FIGS. 31-36, schematic views of a strap retrieval tool in various operational configurations for retrieving and transecting a strap are shown. Accordingly, it is to be understood that the snaring instrument referenced with respect to FIGS. 31-36 is for snaring a strap of a hernia repair implant (not shown) disposed in a patient's abdomen, then partially retracting the strap into the instrument, and subsequently transecting the strap so that it may reside in patient tissue.

Figure 31:
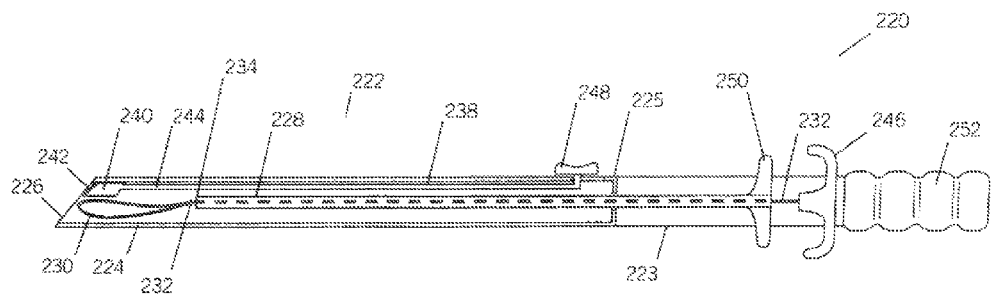
FIGS. 31-36 are schematic views of a strap retrieval tool in various operational configurations retrieving and transecting a strap.

Thus, a snaring instrument 220 includes an elongated tube assembly 222 defining a distal end segment 224 terminating in an open distal end 226 as shown in FIG. 31. The snaring instrument 220 also includes a hypotube 228 that is slidably disposed in the assembly 222 and includes a hypotube handle 250 at an end of the assembly 222 opposite the distal segment 224. The hypotube handle 250 is connected to the hypotube 228 at an end of the hypotube 228 closest to a proximate end 225 of a proximate segment 223 of the assembly 222. The hypotube handle 250 may be used to slide the hypotube 228 as set forth herein. In addition, a loop 230 connected to a loop line 232 is disposed in the hypotube 228. The loop 230 and loop line 232 may be made of, e.g., monofilament. Note that a stabilizer/gripping handle 252 may also be connected to the assembly 222 to, e.g., stabilize the assembly 222 as a physician executes any of the other motions described herein, such as the sliding and cutting motions.

Figure 32:
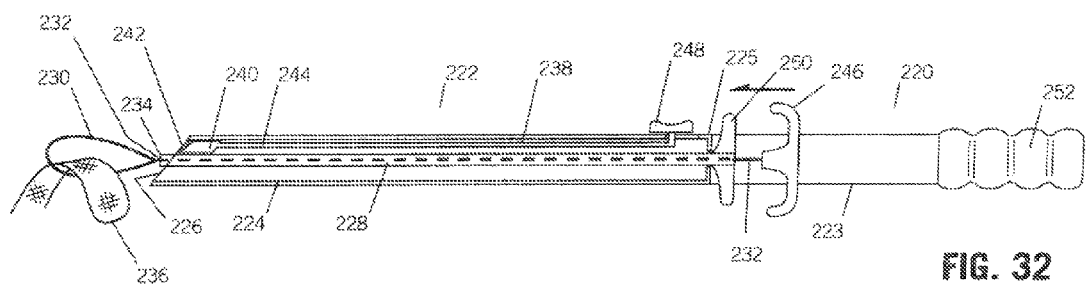

Furthermore, note that the loop 230 is disposed at a distal end 234 of the hypotube 228 such that pushing the hypotube 228 distally in the assembly 222 toward the distal end 226 using, e.g., the handle 250 pushes the loop 230 out of the open distal end 234. This may be appreciated from FIGS. 31 and 32. FIG. 31 shows the loop line within the assembly 222 and the handle 250 of the hypotube 228 relatively more distanced from the distal end 224 than in FIG. 32. FIG. 32 shows the loop 230 pushed out of the distal end 234. Note that the handle 250 is relatively closer to the distal end 224 in FIG. 32 than the handle 250 was in FIG. 31 since it, and hence the hypotube 228, have been pushed toward the distal end 224 such that the loop 230 at least partially protrudes from the distal end 224.

Figure 33:
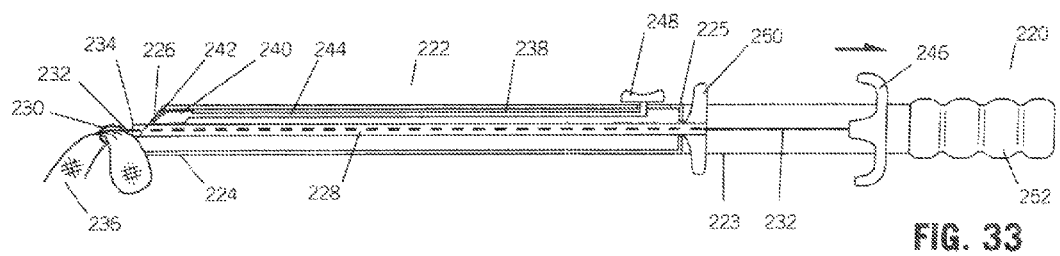

Even further, note that pulling on the loop line 232 cinches the loop 280 against the distal end 234 of the hypotube 228 to shrink the loop 230. As may be appreciated from FIG. 33, a strap 236 of a hernial implant is cinched by the loop 230 when the loop line 232 is pulled using, e.g., a cinch handle 246 connected to an end of the loop line 232 opposite the end of the line 232 having the loop 230. As shown in FIG. 33, the cinch handle 246 is proximate to the proximate end 225 of the proximate segment 223.

Continuing in cross-reference to FIGS. 31-36, the assembly 222 also includes a cutter guard shaft 238. It is to be understood that the cutter guard shaft 238 is slidably disposed in the assembly 222 and includes a cutter guard/cover 240 on a distal end 244 of the shaft 238. The cutter guard 240 may thus abut and/or cover a cutter 242 formed with a cutting edge such as, but not limited to, a blade and/or sharp pointed member. As may be appreciated from FIGS. 31-36, the cutter 242 is positioned inside the assembly 222 at or near the distal end 224. Accordingly, note that the guard shaft 238 is slidably movable within the assembly such that the cutter guard 240 may cover and hence guard the cutter 242 when, e.g., the cutter is not being used for transecting a strap in accordance with present principles, but may nonetheless expose the cutter 242 when desired to transect a strap.

Figure 34:
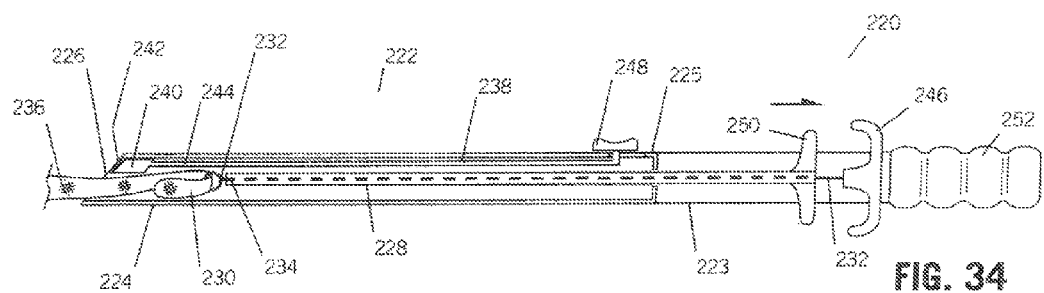

Thus, as may be appreciated from FIG. 34, the hypotube 228 has been pulled toward the proximate end 225 such that the loop 230 has been retracted at least partially into the distal segment 224 and hence the strap 236, being cinched by the loop 230, has also been retracted at least partially into the distal segment 224. Again, note that one or both of the hypotube 228 and loop line 232 may be pulled using their respective handles 250 and 246 to retract the loop 230 at least partially into the distal segment 224.

Further, note that the cutter guard shaft 238 is movable by manipulating a cutter shaft handle 248. Manipulation of, e.g., the assembly 222 and/or loop line 232 having the cinched loop 230, and hence the strap 236, may serve to position the now tensioned strap 236 such that the cutter 242 may transect the strap. This may be accomplished by, e.g., moving the strap 236 at least somewhat linearly and/or laterally across the cutter 242 to facilitate transection of the strap 236. Other motions may be used, such as, but not limited to, exerting angular motion (e.g., twisting) on the assembly 222 to transect the strap 236. However, it is to be understood that still other motion may be employed to transect a portion of the strap 236, such as other rotational motions.

Figure 35:
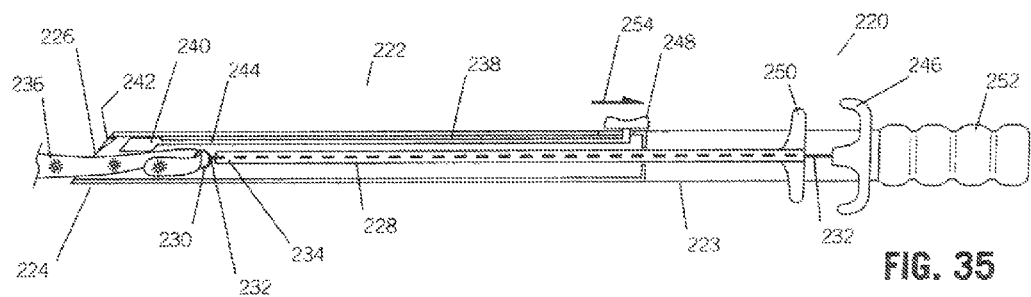

Thus, as shown in FIG. 35 a motion arrow 254 illustrates that the handle 248 has been pulled longitudinally toward the proximate end 225 (and may even be pulled beyond the proximate end 225, if desired) such that the cutter guard shaft 238 and hence the cutter guard 240 are pulled longitudinally away from the cutter 242 at the distal end 226. Note that also as shown in FIG. 35 (as well as FIG. 34), the strap 236 has been cinched by the loop 230 and retracted into the tube assembly 222 using the loop line so that it may be positioned within the assembly 222 to be transected.

Figure 36:
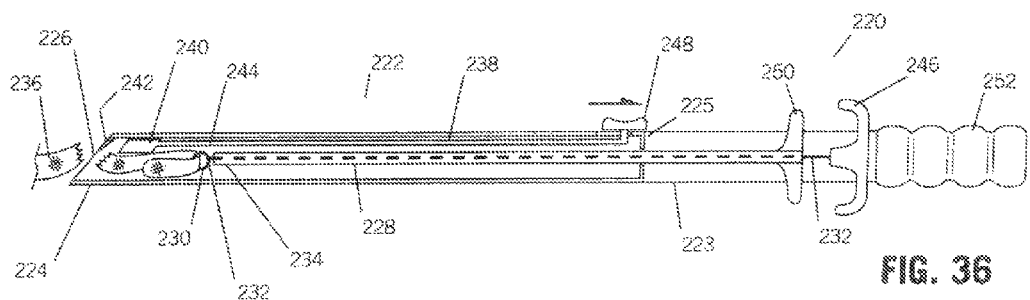

Then, as shown in FIG. 36, the strap 236 may be transected by affecting, e.g., angular motion on the handle 252 to thereby rotate the assembly 222 and hence the cutting edge 242 to thereby transect a portion of the strap 236. The remaining portion of the strap 236 connected to the hernial implant may then be withdrawn from the assembly 222, e.g., by way of tension from the hernial implant, when a physician moves the assembly 222 away from the implant, etc.

Though not shown, note that in other embodiments, a cutter may additionally or alternatively be positioned on the distal end 244 of the shaft 238. In such an embodiment, linear motion, angular motion, etc., by the shaft 238 could be used by manipulating the handle 248 to transect the strap 236 within the assembly 222.

Figure 37:
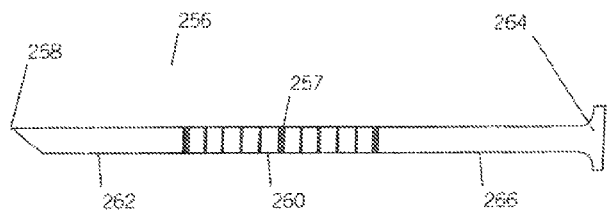
FIG. 37 shows a tunneling cannula with a sharp piercing distal tip.

Continuing the detailed description in reference to FIG. 37, a hollow tunneling cannula 256 that may create a channel, path, and/or tunnel in accordance with present principles is shown. To more easily establish a channel/path, the tunneling cannula 256 has a sharp piercing distal tip 258 at a distal end 262 that may be beveled, yet note that it is still substantially hollow. An elongated shaft 260 of the cannula 256 is understood to be rigid in exemplary embodiments. Even further, the cannula 256 has a receiver 264 at a proximate end 266 to facilitate receipt of the instruments of FIGS. 38 and 39 (which will be described shortly) and guide them into and through the interior of the hollow cannula 256. Note that the receiver 264 may include a seal (now shown) in accordance with present principles to prevent leakage of insufflation gas. Depth markings 257 are also shown and may provide a visual indication of the length of the channel/path under the skin.

Figure 38:
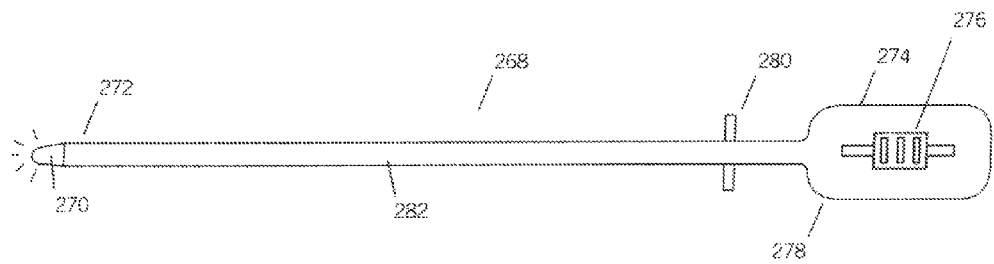
FIG. 38 shows an illuminating cannula that can be advanced through the tunneling cannula of FIG. 37 to illuminate tissue below the surface of the skin which can be perceived by the surgeon for purposes of establishing a position at which a strap insertion tool can be advanced into the patient.

FIG. 38 shows an illuminating cannula 268 that can be advanced through the tunneling cannula 256 of FIG. 37 to illuminate tissue below the surface of a patient's skin, which can be perceived by, a physician for purposes of establishing a position at which a strap insertion/retrieval tool can be advanced into the patient. It is to be understood that the illuminating cannula 268 has a rigid, elongated shaft 282 and a light source 270 at a distal end 272 of the illuminating cannula 268. In exemplary embodiments, the light source 270 is a light emitting diode (LED). The light source 270 may thus illuminate the insufflated abdomen of a patient from inside the patient to provide a visible indication from outside the patient of, e.g., the intramuscular position and/or structure of the patient's abdominal wall being transilluminated through the skin of the abdominal wall. In some embodiments, the light source 270 may be shaped, e.g., as an atraumatic tip such that it serves as an obturator for the tunneling cannula 256 for the purposes of, e.g., blunt dissection as opposed to sharp dissection in accordance with present principles.

Also note that the illuminating cannula 268 includes a handle 274 at a proximate end 278 of the shaft 282 for a physician to grip when, e.g., inserting the illuminating cannula 268 into the tunneling cannula 256. The handle 274 may house a power source (e.g., batteries) to power the light source 270 and may further include an on/off switch 276 to turn the light source 270 on and off as desired. Last, note that the illuminating cannula 268 may also include a stopper 280 if desired so that the illuminating cannula 268 may only be advanced into the tunneling cannula 256 so far, it being understood that the stopper 280 may ride against the receiver 264. Furthermore, the stopper 280 may optionally be movable longitudinally along the shaft 282 so that the illuminating cannula 268 may be advanced into the tunneling cannula 256 as much or little as desired.

Figure 39:
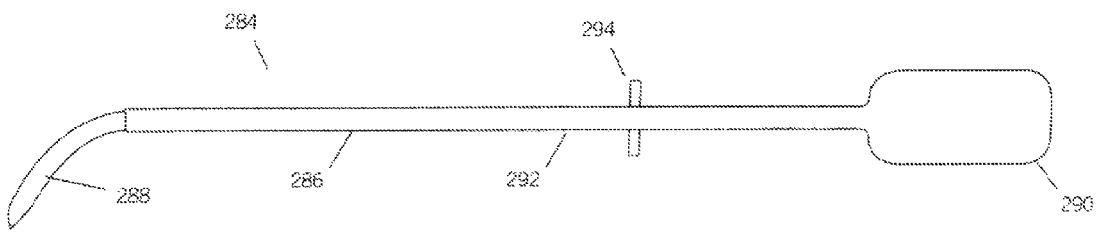
FIG. 39 shows a snare cannula that can be advanced through the tunneling cannula of FIG. 37 to snare a strap of a hernial implant within the abdomen of a patient in accordance with present principles.
Figure 40:
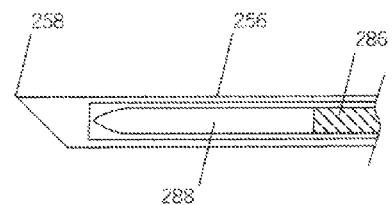
FIGS. 40-42 illustrate a strap insertion tool that can be advanced through the tunneling cannula of FIG. 37 to retrieve a strap.

Now in reference to FIG. 39, a snare cannula 284 that can be advanced through the tunneling cannula 256 of FIG. 37 to snare a strap of a hernial implant within an abdominal cavity of a patient in accordance with present principles is shown. The snare cannula 284 has an elongated, rigid shaft 286 that may be made of steel in exemplary embodiments. The snare cannula 256 also includes a puncturing distal tip 288 that is curved under material bias but is flexible to become at least partially linear when if is inserted through the tunneling cannula 256 as shown in FIG. 40. Note that in exemplary embodiments the tip 288 is made of nitinol or is spring-loaded steel. Regardless, it is to be understood that the distal tip 288 is pushable out of the open distal tip 256 of the tunneling cannula 256 to assume a curved configuration under material bias, as may be appreciated from FIG. 39.

Additionally, the snare cannula 284 also includes a handle 290 at a proximate end 292 of the shaft 286 for a physician to grip when, e.g., inserting the snare cannula 284 into the tunneling cannula 256 and snaring a strap in accordance with present principles. Furthermore, note that the snare cannula 284 may include a stopper 294 if desired so that the snare cannula 284 may only be advanced into the tunneling cannula 256 so far, it being understood that the stopper 294 may ride against the receiver 264. Even further, the stopper 294 may optionally be movable longitudinally along the shaft 286 so that the snare cannula 284 may be advanced into the tunneling cannula 256 as much or little as desired.

FIG. 40 illustrates the snare cannula 284 being advanced through the tunneling cannula 256 of FIG. 37 to retrieve a strap. More specifically, it may be appreciated from FIG. 40 that the snare cannula 284 is advanced through the tunneling cannula 256 from the proximate end 266 of the tunneling cannula 256. Note that the puncturing distal tip 288 is flexible such that it is substantially co-linear with the shaft 286 while being advanced through the tunneling cannula 256.

Figure 41:
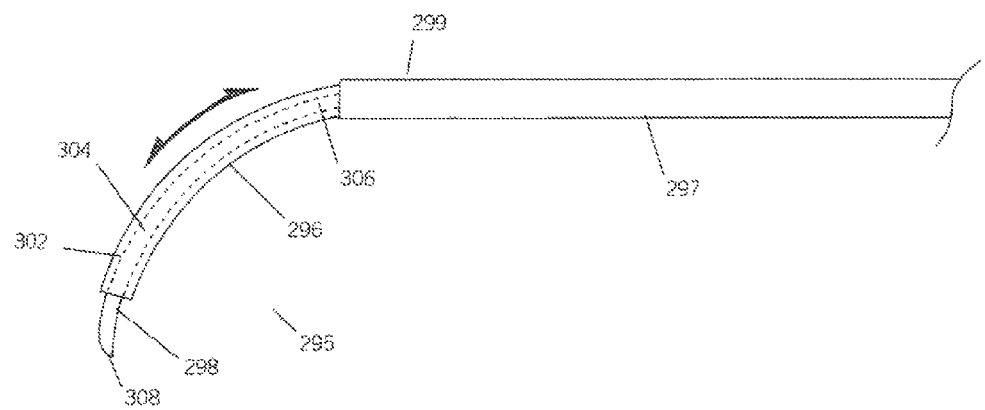
Figure 42:
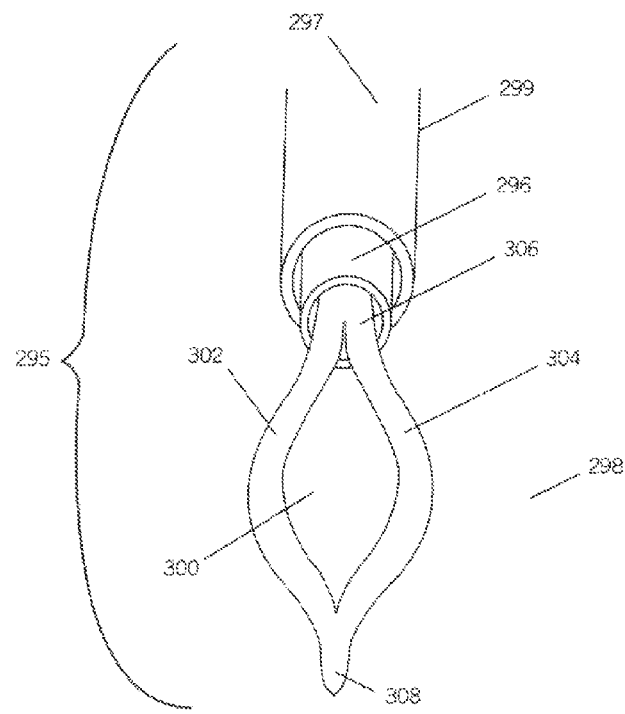

Cross-referencing FIGS. 41 and 42, another exemplary embodiment of a snare cannula in accordance with present principles is shown. Thus, a snare cannula 295 includes a control tube 296 extending at least partially through an elongated, rigid shaft 297, wherein the shaft 297 is understood to at least partially define the snare cannula 295. It is to be further understood that the shaft 297 is substantially similar, in function and configuration to the shaft 286 described above such that it may be advanced through a tunneling cannula, such as, e.g., the tunneling cannula 256 in accordance with present principles. Note that the control tube 296 may be movable under manipulation of e.g., a physician such that it may be retracted at least partially into the shaft 297 and/or protrude at least partially out of a distal end 299 of the shaft 297 when, e.g., at least a portion of a distal end 299 of the shaft 297 is disposed in a patient in accordance with present principles.

Furthermore, a snaring member 298 is at least partially disposed in the control tube 296 and may at least partially protrude from a distal end of the control tube 296. The member 298 may protrude from the control tube 296 when the control tube 296 is manipulated as set forth above, and/or the snaring member 298 may itself be movable within the control tube 296 under manipulation of, e.g., physician such that it may be retracted into or protrude from the control tube 296.

Additionally, as may be appreciated from FIG. 42 in particular, an open eye member 300 may be included at a distal end of the snaring member 298 (e.g., at the distal end/tip of the snaring member 298). The open eye member 300 includes a penetrating tip 308 at a distal end 309 of the open eye member 300. Further, note that both the control tube 296 and snaring member 298 including the open eye 300 may be curved under material bias yet still be flexible to become at least partially linear when inserted through a tunneling cannula in accordance with present principles.

Further describing the open eye member 300, reference is still made to FIG. 42. It may be appreciated from FIG. 42 that a portion of a strap may be positioned through the open eye 300 in accordance with present principles. More specifically, the open eye 300 has two optionally curved members 302 and 304 (in exemplary embodiments the members 302 and 304 may be curved under material bias yet still be manipulable by a physician to snare a strap) that that separate at a proximate end 306 the eye 300 (i.e. the end opposite the tip 308), and then rejoin at the tip 308. In other words, the end 306 is understood to be proximate to the control tube 296 while the tip 308 is understood to be distal to the control tube 296. Regardless, the members 302 and 304 may snare a strap in the configuration shown in FIG. 42, and/or may also be cinched by a physician in accordance with present principles to snare the strap.

Therefore, in accordance with the principles set forth above, it may now be appreciated that the control tube 296 may be retracted its to the shaft 297 after the tip 308 at least partially penetrates a muscle layer of the patient's abdominal wall without the snaring member 298 being retracted with it, thereby further exposing the open eye member 300 and tip 308 such that it may better and/or more easily be used for snaring/retrieving a centering or fixation strap in accordance with present principles. Also note that when the control tube 296 is retracted, the members 302 and 304, if partially disposed within the control tube 296 prior to being retracted, may go from being substantially straight while in the tube 296 to being curved under material bias as shown in FIG. 42. Thus, it may be further appreciated that the eye 300 with members 302 and 304 facilitates strap retrieval since it can capture and/or cinch a strap between the members 302 and 304 under manipulation of a physician, and may be even further facilitated by retracting the control tube 296 as disclosed above.

Figure 43:
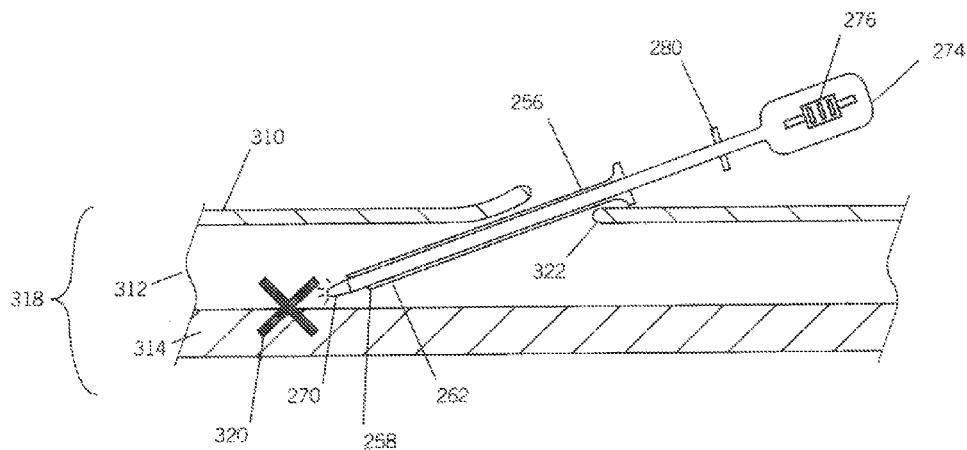
FIGS. 43-45 illustrate steps in the procedure for using the tools of FIGS. 37-42.
Figure 44:
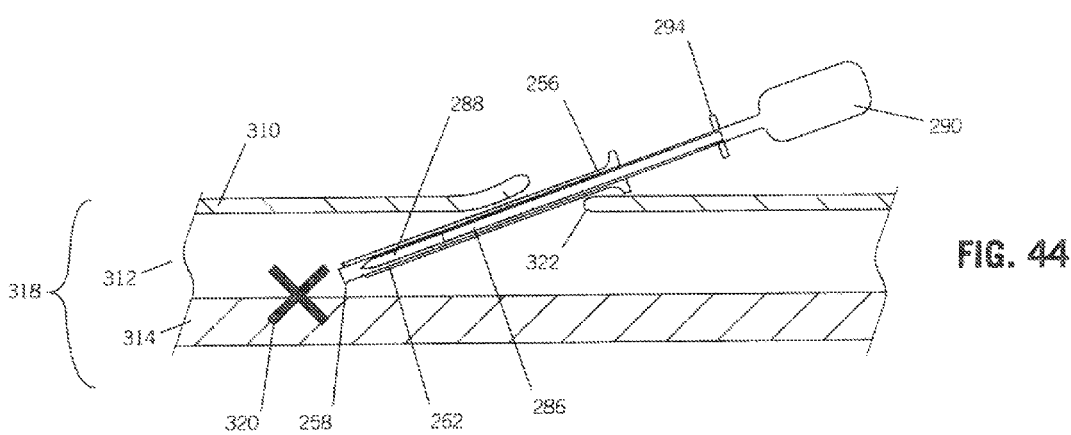
Figure 45:
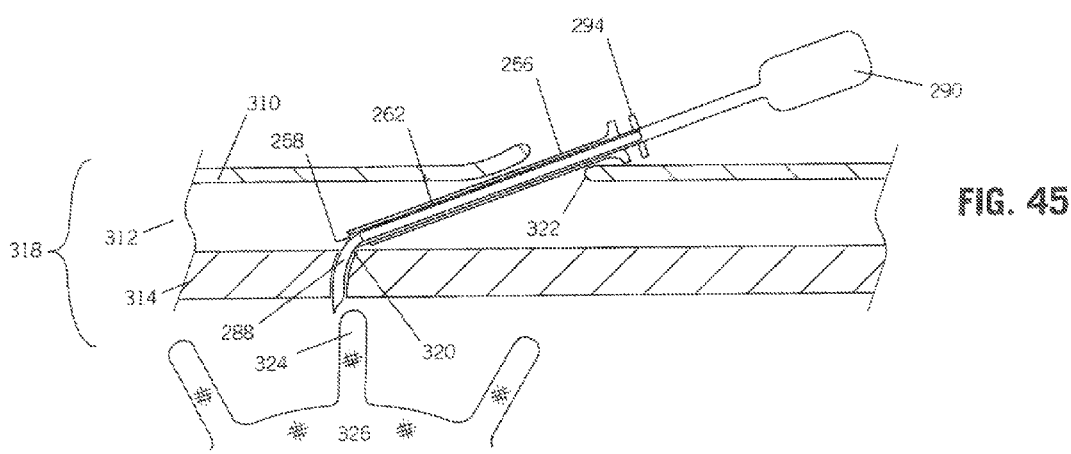

Moving on, FIGS. 43-45 illustrate steps in the procedure for using the tools of FIGS. 37-42. Beginning with FIG. 43, the hollow tunneling cannula 256 described above is shown as being advanced through a single incision site 322 in a patient's skin and into an insufflated abdomen of the patient to form a path. It may also be appreciated from FIG. 43 that the illuminating cannula 268, being advanced through the tunneling cannula 256, is likewise advanced at least partially into the patient's abdominal wall 318, in this case through a skin layer 310 and into the fat layer 312. However, the illuminating cannula 268 and tunneling cannula 256 are notably not advanced into the muscle layer 314.

Accordingly, if may be appreciated from FIG. 43 that the light source 270 of the illumination cannula 268 protrudes from the distal end 262 of the tunneling cannula 256 and trans-illuminates at least a portion of the insufflated abdomen from inside the patient viewable at least through a laparoscope when the light source 270 is powered on. The light source 270 thus provides a visible indication appreciable from outside the patient to help establish a position at which a strap insertion/retrieval tool can be advanced into the patient. As noted above, it is to be understood that the illumination cannula 268 is advanced between a fat layer 312 and a muscle layer 214 of the patient's abdominal wall 318, but not through the muscle layer 314 to a muscle layer piercing location 320, using visualization of light from the light source 270 propagating through the skin.

Next, as shown in FIG. 44, the illumination cannula 268 has been removed from the tunneling cannula 256 and the snare cannula 284 is advanced into the tunneling cannula 256 toward the piercing location 320. The puncturing distal tip 288 of the snare cannula 284 is pushable out of an open distal end of the snare cannula 284. As shown in FIG. 44, the tip 288 is substantially linear while being advanced through the tunneling cannula 256 but assumes a curved configuration under material bias as shown in FIG. 45 once it has been at least partially advanced beyond the distal tip 258. The tip 288 of the snare cannula 284 may then be advanced through the muscle layer 314 and into the insufflated abdomen of a patient to establish a retrieval channel/oath through which a portion of hernial implant 326 can be retrieved such as, e.g., a strap 324. The tip 288 may then be manipulated to retrieve the strap 324.

Now addressing FIGS. 46-49, operational steps and tools for advancing the mesh laparoscopically into a patient are shown. Present principles recognize that the size and/or dimensions of a hernial implant sometimes make it difficult to be advanced into a trocar, which in turn is advanced into the abdomen of a patient. The description of FIGS. 46-49 addresses this concern.

Figure 46:
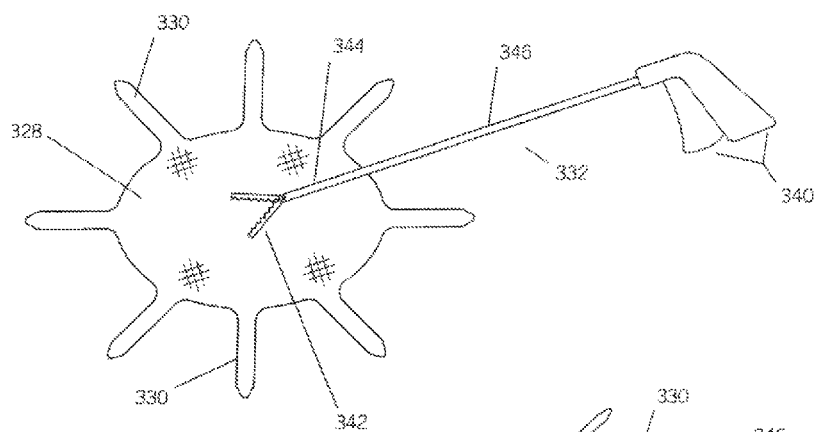
FIGS. 46-49 illustrate operational steps and tools for advancing the mesh laparoscopically into a patient.
Figure 47:
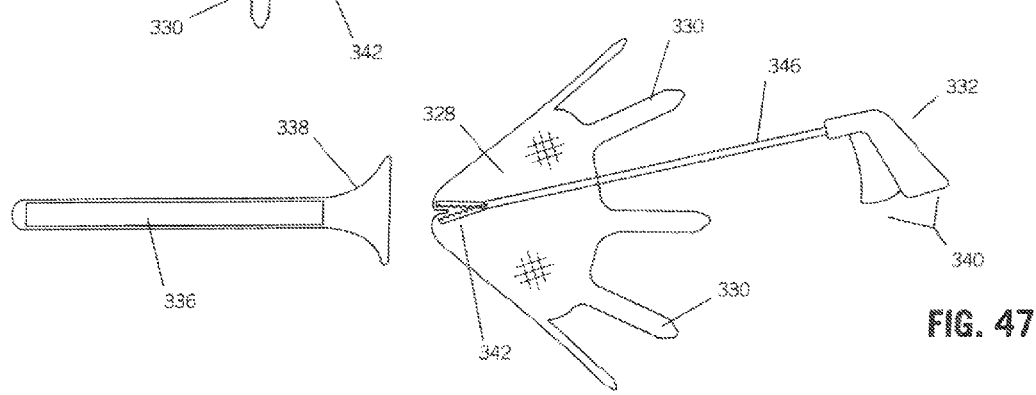

Accordingly, beginning with FIG. 46, a hernial implant 328 having plural straps 330 in accordance with present principles is shown. Note that as shown in FIG. 46, the implant 328 is substantially unfolded when initially grasped by a flexible endoscopic grasper/pusher 332. Note that the implant 328 is grasped at least somewhat centrally by the grasper/pusher 332. The grasper 332 includes a handle 340 and a grasping element 342 at a distal end 344 of a grasper shaft 346 of the grasper 332. The grasping element 342 may be, e.g., a movable grasping jaw, may include a semi-adhesive material, may include hooks, spikes, and/or barbs, etc. It is to be understood that the implant 328 may be advanced into a patient as set forth below after the patient's abdomen is insufflated and laparoscopic access into the abdomen through a surgical trocar assembly (not shown).

Nonetheless, referring back to FIG. 47, a endoscopic grasper 332 is shown. The grasper 332 may grasp and/or receive a center portion of the implant 328. The implant 328 is then pushed into an open proximal funnel 338 holding a flexible hollow sheath 336 therein using the grasper 332. Then as shown in FIG. 48, the implant 328 continues to be pushed further into the funnel 338 and hence into the sheath 336 inside the funnel 338, thus causing the implant 328 to fold inwardly on itself as it enters the sheath 336.

Figure 48:
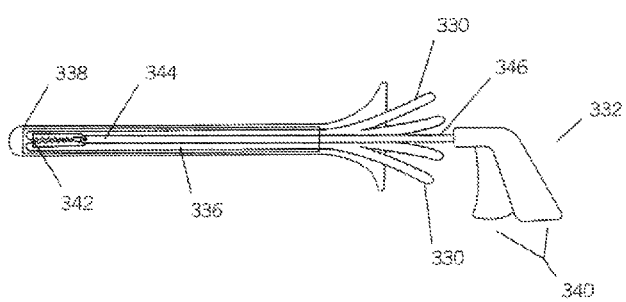
Figure 49:
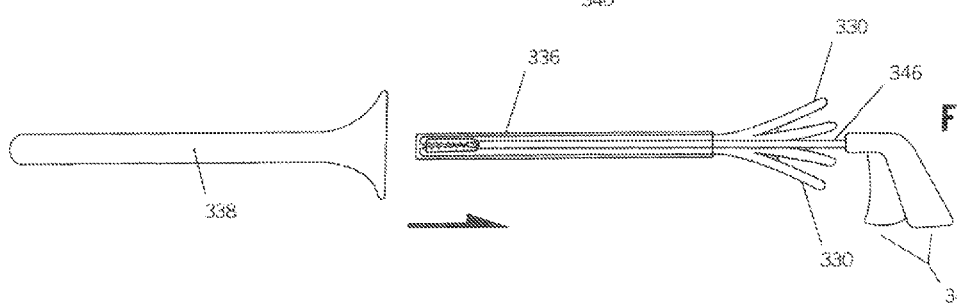

This inward-folding of the implant 328 may be appreciated from both FIGS. 48 and 49. Note that pushing of the implant 328 into the tunnel 338 and sheath 336 may be facilitated using many different motions, including linear motion, oscillating pushing and pulling motion, and/or angular motion such as twisting of the grasper 332 and hence twisting of the implant 328 while being pushed inward.

Thereafter, the sheath 336 having the implant 328 may be removed from the funnel 338 using, e.g., the grasper 332 so that it may be advanced into a surgical trocar assembly which may in turn be advanced into the insufflated abdomen of a patient. The implant 328 may then be removed from the sheath 336 while inside the abdominal cavity of the patient so that it may be unfolded to cover a hernia defect in accordance with present principles. It may be thus appreciated from the description of FIGS. 46-49 that the implant 328 may more easily be advanced into the abdomen of a patient when folded into a sheath as set forth herein.

However, note that in other embodiments, the sheath 336 and funnel 338 may be integrated to form a unitary body such that both the sheath 336 and funnel 338 are not removable from each other and the unitary body may be advanced into a patient using a trocar assembly. In still other embodiments, a sheath 336 need not be used and the implant 328 may simply be advanced into an open ended funnel which in turn is advanced into the patient in accordance with present principles.

Figure 50:
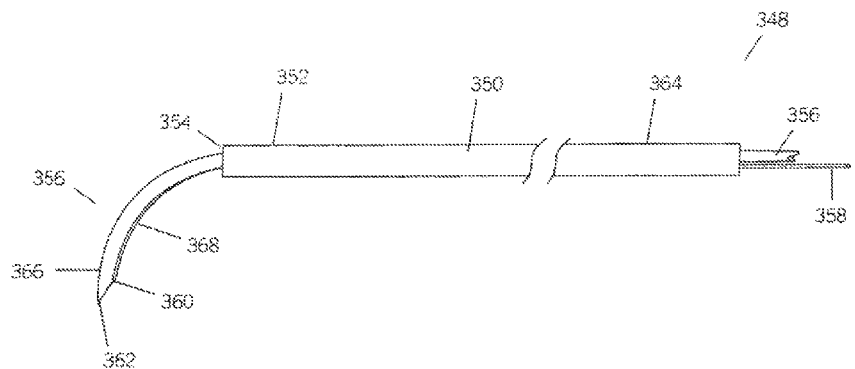
FIGS. 50-52 are schematic views of a fifth strap retrieval element that can be used in the strap retrieval tool of FIGS. 19-23.
Figure 51:
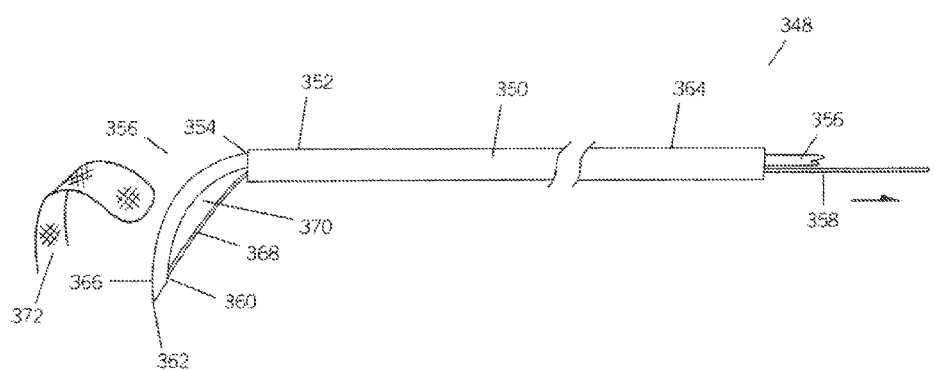
Figure 52:
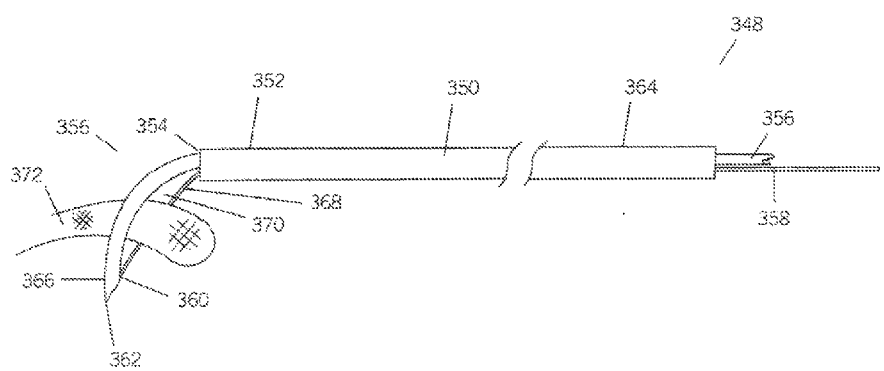

Now in cross-reference to FIGS. 50-52, schematic views of another strap retrieval element that may be used in accordance with present principles is shown. Thus, a snaring instrument 348 that may be used for snaring a strap of a hernia repair implant disposed in a patient's abdomen includes an elongated tube assembly 350 that defines a distal end segment 352 terminating at an open distal end 354. The instrument also includes a snare member 356 extending out of the distal end 352 of the assembly 350. In addition, a cord 558 is attached to the snare member 356 at a location 360 understood to be at or near a distal end 362 of a distal segment 366 of the snare member 356. It is to be understood that the distal end 362 may in some embodiments act as a piercing element in accordance with present principles.

Note that both the snare member 356 and cord 358 may extend front the distal end 354 through the assembly 350 to a proximal end segment 364 of the assembly 350. Also note that the distal segment 366 of the snare member 356 extending out of the distal end 354 may be curved, e.g., under material bias and/or spring bias. Even further, a distal segment 368 of the cord 358 also extending out of the distal end 354 may be curved, e.g., under material and/or spring bias, and/or nonetheless assume a degree of curvature substantially similar to the degree of curvature of the distal segment 366. This may be appreciated from FIG. 50, where the distal segment 366 and distal segment 368 have a similar degree of curvature and are proximate to each other.

As may be appreciated by comparing FIG. 50 with FIG. 51, the distal segment 366 of the snare member 356 and the distal segment 368 of the cord 358 are movable between a closed configuration (FIG. 50) as described above (e.g., the distal segments 366 and 368 having a similar degree of curvature and being proximate to each others and an open configuration (FIG. 51). As may be appreciated from the open configuration of FIG. 51, the distal segment 366 of the snare member 356 and the distal segment 368 of the cord 358 are distanced from each other to establish a gap and/or loop 370.

Figure 53:
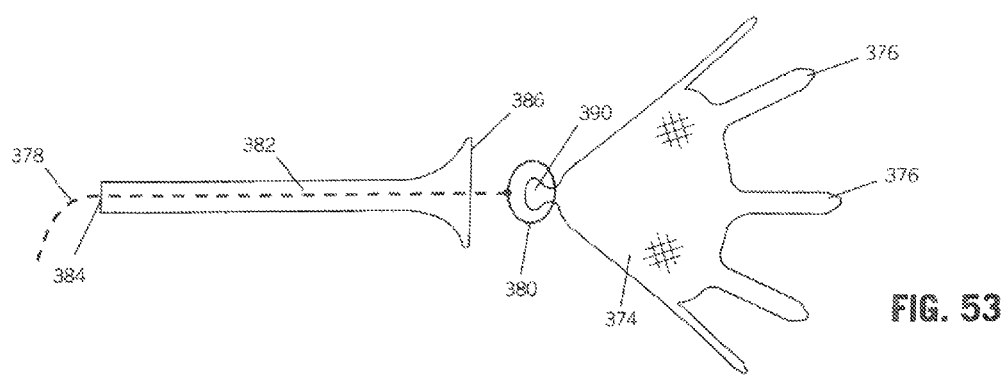
FIGS. 53-55 illustrate operational steps and tools for advancing the mesh laparoscopically into a patient.

Then, as may be appreciated by FIG. 52, the gap 370 allows a strap 372 to pass through the loop to be snared and/or cinched between the distal segments 366 and 368. Note that the distal segments 366 and 368 are movable between the open and closed configurations by, e.g., manipulating tension in the cord 358. Thus, for example, the cord 358 may have relatively less tension exerted on it as shown in FIG. 50 and thus may conform to a degree of curvature similar to the degree of curvature of the distal segment 366, and also be proximate to the segment 366. Yet as shown in FIGS. 51 and 53, the cord 358 may have relatively more tension exerted on it when pulled by, e.g., a physician from the proximal segment 364 of the assembly 350 to thereby pull the distal segment 368 of the cord 358 away from the distal segment 366 of the snare member 356 to thus cause the distal segment 368 to have less of a degree of curvature than the distal segment 366 and create the gap 370. Also note that in some embodiments, tension in the cord 358 may cause the distal segment 366 to have a greater degree of curvature such that it may bend under the tension from the cord 358.

Then, after the strap 372 has passed at least partially through the gap 370 as shown in FIG. 52, tension in the cord 358 may be eased and/or released such that the distal segment 368 of the cord 358 again becomes proximate to the distal segment 366 and also assumes a degree of curvature similar to the degree of curvature of the distal segment 366. Retrieval of distal segment 366 and cord 358 into tube assembly 350 causes the strap 373 to become trapped against distal end 354 and cinched for retrieval in accordance with present principles.

Figure 54:
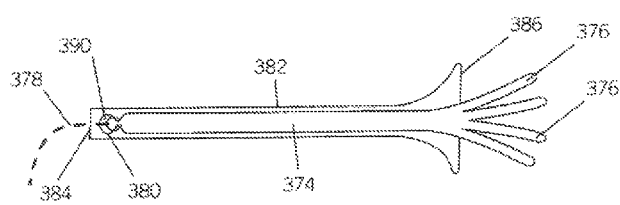
Figure 55:
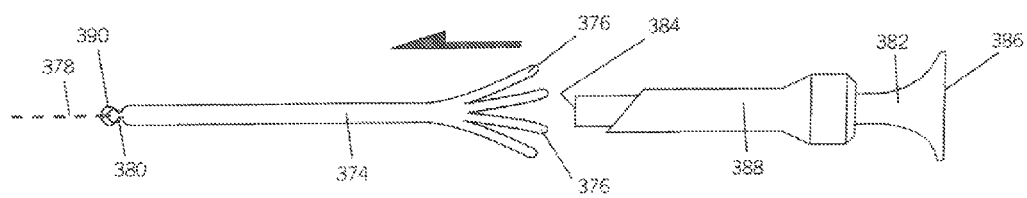

Reference is now made to FIGS. 53-55, which illustrate operational steps and tools for advancing the mesh laparoscopically into a patient. These operational steps and tools may be used in accordance with present principles, but are understood to be particularly useful when an implant is too voluminous to be used with the operational steps of FIGS. 46-49 when, e.g., a grasper used in accordance with those operational steps and tools may not be able to concurrently fit inside a tunnel with a relatively more voluminous implant.

Accordingly, FIG. 53 shows an implant 374 with plural straps 376, where the implant 374 and straps 376 are understood to be similar in function and configuration to the implants and straps described above. A cord and/or string 378 are also shown in FIG. 53. A loop 380 may be formed with the cord 378 and may grasp a center portion 390 of the implant 374 by, e.g., cinching it.

Still in reference to FIG. 53, the cord 378 extends away from the loop 380 and into an open proximal funnel 382, and may in fact extend through the funnel 382 and out of a distal end 284 of the funnel 382. Thus, the loop 380 may cinch the center portion 390 and then, e.g., a physician may begin pulling the cord 378 and hence the center portion 390 of the implant 374 into a proximal end 386 of the funnel 382. It is to be understood that the proximal end 386 has a wider diameter than the end 384 to thereby establish the funnel shape.

Then, as may be appreciated from FIG. 54, the implant 374 continues to be pulled into the funnel 382, thereby causing the implant 374 to fold inwardly on itself as it progressively enters the funnel 382. In some embodiments, the implant 374 may assume a cigar-like shape and may be advanced more easily into the funnel 382 by exerting, e.g., an angular and/or twisting motion on the implant 374 as it is advanced into the funnel 382. Once substantially advanced into the funnel 382 as shown in FIG. 54, the funnel 382 and hence the implant 374 may be advanced into a trocar assembly that itself is advanced into the insufflated abdomen of a patient.

Accordingly, as shown in FIG. 55, the cord 378 may then be pulled inside the patient's abdomen to pull the implant 374 through the funnel 382 such that it completely exits the distal end 384 and exits a trocar 388 at least partially surrounding the funnel 382. Once advanced out of both the funnel 382 and trocar 384, the implant 374 may unfold under material bias and/or be unfolded by, e.g., a physician for positioning to cover a hernial defect in accordance with present principles.

Last, note that in other exemplary embodiments, the cord 378 may not be used. Instead, the loop 380 may be secured to the center portion 390 and then a surgical tool and/or cord may be advanced from the end 284 through the funnel 382 to grasp the loop 380. The surgical tool and/or cord may then be advanced back out of the end 284, thereby pulling the implant 374 through the funnel 382 in accordance with present principles. Also, the cord 378 may be removed after loading into funnel 382 and once inside the trocar 384, an instrument can be used to push the implant 374 into the patient's abdomen.

Figure 56:
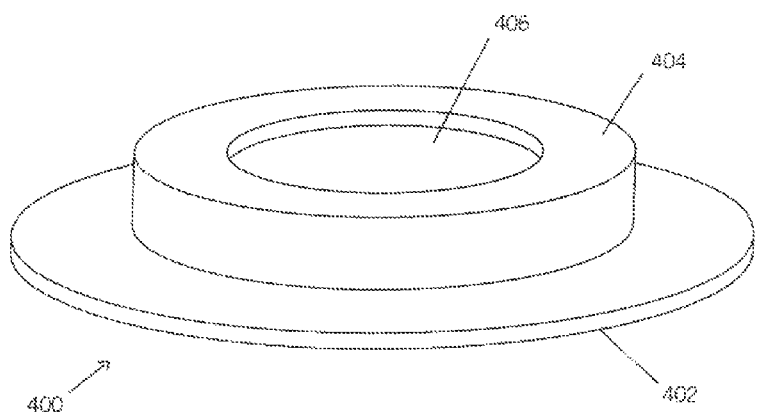
FIGS. 56 and 57 are perspective and partial cross-sectional views, respectively, of an alternate skin seal through which strap retrieval tools and straps can be advanced without causing an undue loss of laparoscopic insufflation of the abdomen.
Figure 57:
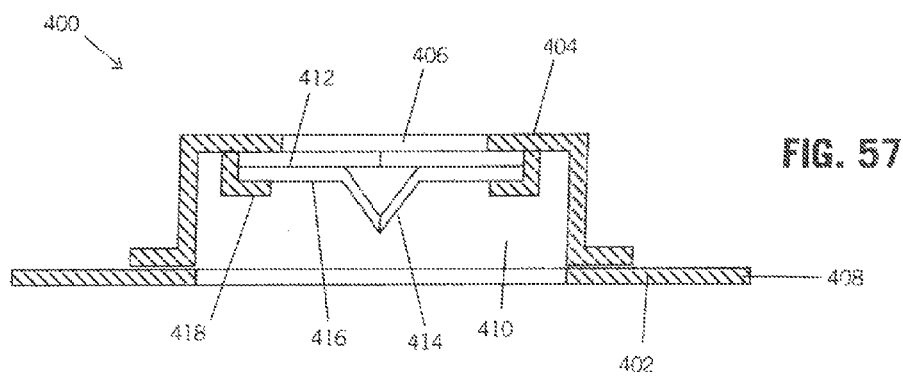

Now in cross-reference to FIGS. 56 and 57, a pneumatic seal 400 is shown which in all essential respects is identical in configuration and operation to the seal 56 shown in FIGS. 9 and 10, with the following exceptions. The seal 400 is formed as a disk with a flat top so that it appears rectangular in cross-section as shown in FIG. 57. A disk-shaped patient adhesion side 402 is formed opposite to a flat top 404, and an opening 406 may be centrally formed in the top 404 as shown. The opening 406 may be covered by a membrane if desired. The adhesion side 402 may be made of an acrylic material in exemplary embodiments and may be disposed on an adhesive pad 408 as shown.

The seal 400 includes a sealant chamber 410 which may be empty or which may contain sealant according to description above in relation to FIGS. 9 and 10. Additionally, disposed in the chamber 410 just below the top is a valve 412 such as the duckbill valve shown, in which sides 414 taper downwardly toward each other to essentially establish a one-way valve from top to bottom through which a puncturing instrument may be advanced. The sides 414 may be circumscribed by a disk-shaped valve skirt 416 formed integrally with the sides 414, and the skirt can be trapped between the top 404 and a circular flange 418 formed around the periphery of the chamber 410 to hold the valve 412 in place within the chamber 410.

While the particular IMPLANT FOR HERNIA REPAIR is herein shown and described in detail, it is to be understood that the subject matter which is encompassed by the present invention is limited only by the claims.

What is claimed is:

1. Method for laparoscopic implantation of a hernia repair implant having fixation straps with respective ends, comprising:
    laying the implant or a pattern thereof on a patient's abdomen;
    indicating on the patient's abdomen a strap end retrieval piercing location for at least some respective strap ends;
    advancing the implant into the patient's insufflated abdomen through a trocar;
    unfolding the implant inside the patient; and
    using the piercing locations indicated on the patient's abdomen, retrieving straps up into the patient's tissue by advancing a snaring instrument into the patient through a piercing location, snaring the end of the strap, and pulling the strap outwardly.

2. The method of claim 1, wherein the strap end is pulled completely out of the patient.

3. The method of claim 1, wherein the strap end is pulled outwardly and allowed to reside in subcutaneous tissue of the patient without pulling the strap end all the way out of the patient.

4. The method of claim 1, wherein the strap end is pulled completely out of the patient, and method comprises tenting the patient's abdomen to cause the strap end to slip below the surface of the patient's skin such that the strap end thereafter is allowed to reside in subcutaneous tissue of the patient.

5. The method of claim 1, wherein the step of indicating on the patient's abdomen a strap end retrieval piercing location includes using ink to indicate the piercing location.

6. The method of claim 1, wherein the step of indicating on the patient's abdomen a strap end retrieval piercing location includes disposing a pneumatic seal on the abdomen to indicate the piercing location.

7. The method of claim 1, wherein the step of indicating on the patient's abdomen a strap end retrieval piercing location includes indicating a piercing location that is laterally distanced from the strap end when the strap end is inside the abdomen such that the piercing instrument is advanced laterally through a portion of tissue into the abdomen and likewise the strap after being pulled away from the abdomen resides in a lateral orientation relative to an anterior-posterior dimension defined by the patient's body.

8. The method of claim 1, wherein the step of using the piercing locations indicated on the patient's abdomen to retrieve straps includes forming a curved path through tissue of the patient by advancing a curved piercing instrument through a piercing location and into the abdomen to establish a curved retraction path, and then advancing the snaring instrument into the patient along the curved path.

9. The method of claim 1, comprising illuminating an abdominal space inside the patient such that light from the space propagates through the patient's skin to give visual indication outside the patient of interior tissue of the patient including blood vessels to facilitate advancing the piercing instrument into the patient.

10. Method for laparoscopic implantation of a hernia repair implant having fixation straps with respective ends, comprising:
- advancing the implant into the patient's insufflated abdomen through a trocar;
- unfolding the implant inside the patient;
- retrieving a strap up into the patient's tissue by advancing a snaring instrument into the patient along a path that is not parallel to an anterior-posterior dimension defined by the patient's body;
- snaring the end of the strap using the snaring instrument;
- pulling the strap outwardly along the path such that the strap is disposed in the patient in an orientation that is not parallel to the anterior-posterior dimension;
- disengaging the instrument from the strap such that at least a segment of the strap remains implanted in the patient in the orientation that is not parallel to the anterior-posterior dimension; and
- not suturing or otherwise affixing the strap to the patient.

11. Method for laparoscopic placement of a hernia repair implant, comprising:
- advancing a hollow tunneling catheter through a patient's skin into an insufflated abdomen of a patient to form a path;
- advancing an illumination catheter through the tunneling catheter, the illumination catheter having a light source thereon to illuminate the insufflated abdomen from inside the patient to provide a visible indication from outside the patient, the illumination catheter being advanced between a fat layer and a muscle layer but not through the muscle layer to a muscle layer piercing location under visualization of light from the light source propagating through the skin;
- removing the illumination catheter from the tunneling catheter and advancing a snare catheter through the tunneling catheter to the piercing location, the snare catheter having a puncturing distal segment pushable out of an open distal end of the tunneling catheter to assume a curved configuration under material bias; and
- advancing the puncturing distal segment through the muscle layer into the insufflated abdomen to establish a retrieval path through which a portion of the implant can be retrieved.

12. The method of claim 11, wherein the puncturing distal segment is formed with an open eye through which a portion of the mesh can be positioned.

\* \* \* \* \*